United States Patent [19]

Takasugi et al.

[11] Patent Number: 5,037,824

[45] Date of Patent: Aug. 6, 1991

[54] N-CONTAINING HETEROCYCLIC COMPOUNDS, COMPOSITIONS AND USE

[75] Inventors: Hisashi Takasugi; Atsushi Kuno, both of Osaka; Hiroyoshi Sakai, Uji, all of Japan

[73] Assignee: Fujisawa Pharmaceutical Company, Ltd., Osaka, Japan

[21] Appl. No.: 489,536

[22] Filed: Mar. 7, 1990

[30] Foreign Application Priority Data

Mar. 10, 1989 [GB] United Kingdom ............... 8905526

[51] Int. Cl.$^5$ .................. A61K 31/535; A61K 31/54; C07D 413/12; C07D 417/12
[52] U.S. Cl. ............................. 514/227.8; 514/237.2; 514/252; 514/318; 514/340; 514/341; 514/343; 544/58.6; 544/131; 544/365; 546/194; 546/275; 546/278; 546/279; 546/281
[58] Field of Search ...................... 544/58.6, 131, 365; 546/194, 275, 278, 279, 281; 514/237.2, 252, 318, 340, 341, 343, 227.8

[56] References Cited

U.S. PATENT DOCUMENTS 4,831,030  5/1989  Takasugi et al. ............ 514/252
4,857,527  8/1989  Takaya et al. ............... 544/131
4,990,507  2/1991  Takaya et al. ............... 544/131

Primary Examiner—Robert W. Ramsuer
Attorney, Agent, or Firm—Oblon, Spivak, McClelland, Maier & Neustadt

[57] ABSTRACT

The invention relates to cardioprotective compounds of the formula:

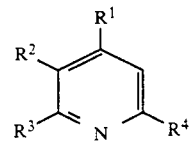

wherein $R^1$, $R^2$, $R^3$ and $R^4$ are moieties as described in the specification.

6 Claims, No Drawings

N-CONTAINING HETEROCYCLIC COMPOUNDS, COMPOSITIONS AND USE

This invention relates to new N-containing heterocyclic compounds. More particularly, this invention relates to new N-containing heterocyclic compounds and their salts which possess a reducing effect of reperfusion injury and cardioprotective effect such as an improving or enhancing effect of the depressed cardiac metabolism, to processes for the preparation thereof and to pharmaceutical compositions comprising the same as an active ingredient.

The N-containing heterocyclic compounds of this invention are represented by the following general formula [I]:

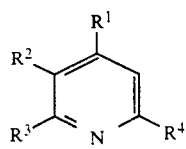

wherein $R^1$ is aryl optionally substituted with substituent(s) selected from the group consisting of nitro, cyano, halogen, halo(lower)alkyl, lower alkoxy, lower alkylsulfonyl, lower alkylsulfonylamino, amino, lower alkanoyl, sulfamoyl and lower alkylsulfamoyl; or a heterocyclic group optionally substituted with substituent(s) selected from the group consisting of nitro, cyano, lower alkanoyl and hydroxy(lower)alkyl;

$R^2$ is cyano; lower alkanoyl; carboxy; esterified carboxy; hydroxy(lower)alkyl; carbamoyl substituted with heterocyclic(lower)alkyl; amino optionally substituted with substituent(s) selected from the group consisting of heterocyclic(lower)alkanoyl and halo(lower)alkanoyl; or N-containing heterocycliccarbonyl optionally substituted with lower alkyl;

$R^3$ is lower alkyl; and $R^4$ is aryl optionally substituted with substituent(s) selected from the group consisting of nitro, hydroxy and halogen; carboxy; esterified carboxy; a heterocyclic group; lower alkyl; or carbamoyl substituted with heterocyclic(lower)alkyl;

provided that $R^4$ is aryl substituted with substituent(s) selected from the group consisting of nitro and hydroxy; carboxy; esterified carboxy; a heterocyclic group; lower alkyl; or carbamoyl substituted with heterocyclic(lower)alkyl; when $R^1$ is phenyl substituted with nitro.

The object compound [I] or its salt can be prepared by processes as illustrated in the following reaction schemes.

Process 1

$R^1-CH=CH-CO-R^4 +$

[II]
or its salt

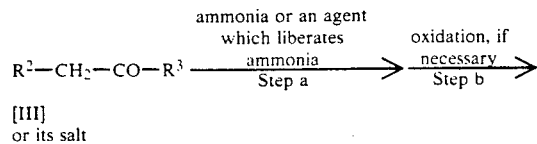

-continued

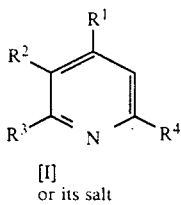

[I]
or its salt

Process 2

$R^1-CH=CH-CO-R^4 +$

[II]
or its salt

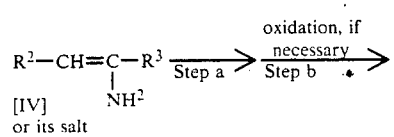

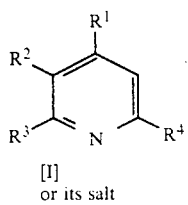

[I]
or its salt

Process 3

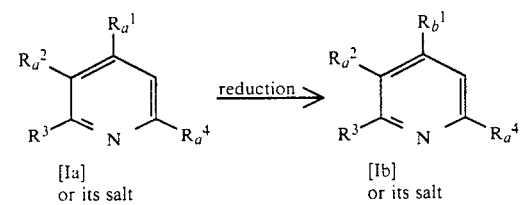

Process 4

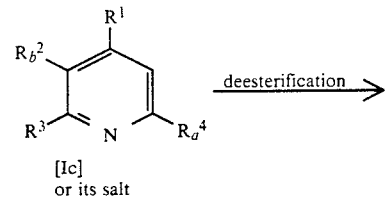

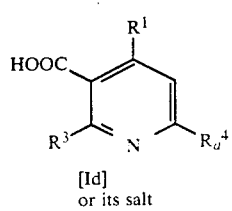

[Id]
or its salt

Process 5

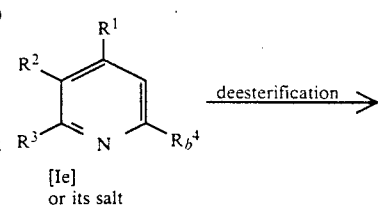

-continued

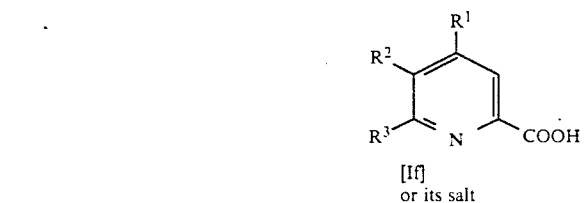

[If]
or its salt

Process 6

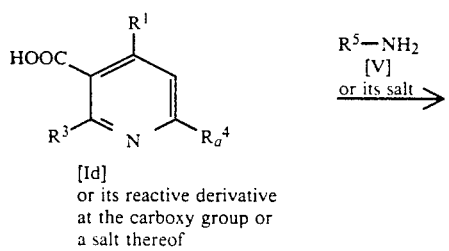

[Id]
or its reactive derivative
at the carboxy group or
a salt thereof

R⁵—NH₂
[V]
or its salt
⟶

R⁵—HNOC

[Ig]
or its salt

Process 7

[If]
or its reactive derivative
at the carboxy group or
a salt thereof

R⁵—NH₂
[V]
or its salt
⟶

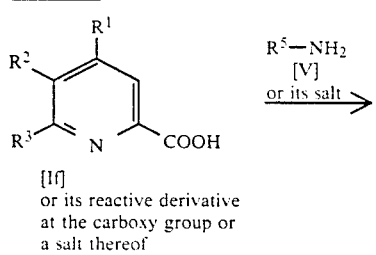

[Ih]
or its salt

Process 8

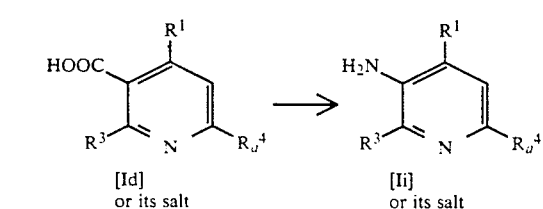

[Id]
or its salt → [Ii] or its salt

Process 9

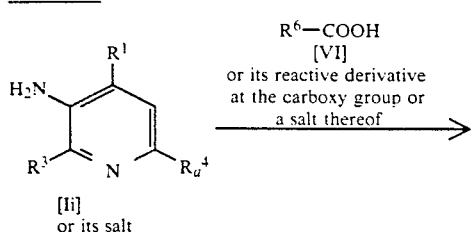

[Ii]
or its salt

R⁶—COOH
[VI]
or its reactive derivative
at the carboxy group or
a salt thereof
⟶

-continued

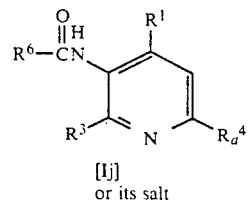

[Ij]
or its salt

Process 10

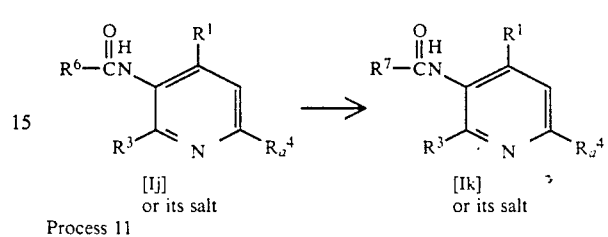

[Ij]
or its salt → [Ik] or its salt

Process 11

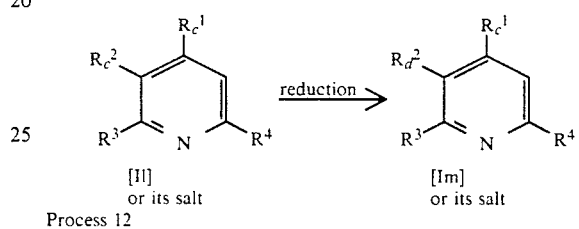

[Il]
or its salt
reduction→
[Im]
or its salt

Process 12

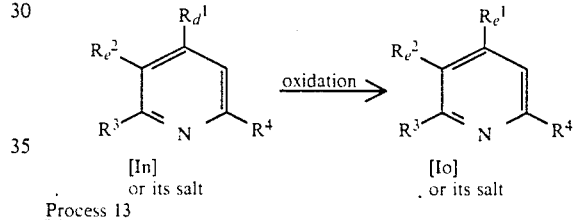

[In]
or its salt
oxidation→
[Io]
or its salt

Process 13

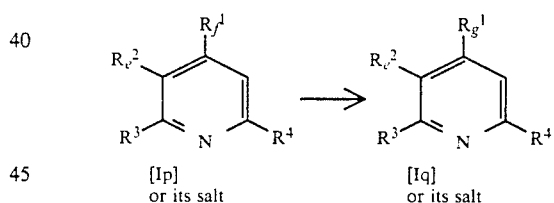

[Ip]
or its salt
→
[Iq]
or its salt wherein
$R_a^1$ is aryl substituted with cyano,
$R_b^1$ is aryl substituted with formyl,
$R_a^2$ is hydroxy(lower)alkyl; carbamoyl substituted with heterocyclic(lower)alkyl; amino optionally substituted with substituent(s) selected from the group consisting of heterocyclic(lower)alkanoyl and halo(lower)alkanoyl;
$R_a^4$ is aryl optionally substituted with substituent(s) selected from the group consisting of nitro, hydroxy and halogen; a heterocyclic group; lower alkyl; or carbamoyl substituted with heterocyclic(lower)alkyl;
$R_b^2$ is esterified carboxy,
$R_b^4$ is esterified carboxy,
$R^5$ is heterocyclic(lower)alkyl,
$R^6$ is halo(lower)alkyl,
$R^7$ is N-containing heterocyclic(lower)alkyl,
$R_c^1$ is aryl optionally substituted with substituent(s) selected from the group consisting of nitro, cyano, halogen, halo(lower)alkyl, lower alkoxy, lower alkylsulfonyl, amino, sulfamoyl and lower alkylsulfamoyl;

or a heterocyclic group optionally substituted with substituent(s) selected from the group consisting of nitro, cyano and hydroxy(lower)alkyl;

$R_c^2$ is lower alkanoyl, $R_d^2$ is hydroxy(lower)alkyl, $R_d^1$ is a heterocyclic group substituted with hydroxy(lower)alkyl, $R_e^1$ is a heterocyclic group substituted with lower alkanoyl, $R_e^2$ is cyano; lower alkanoyl; carboxy; esterified carboxy; carbamoyl substituted with heterocyclic(lower)alkyl; amino optionally substituted with substituent(s) selected from the group consisting of heterocyclic(lower)alkanoyl and halo(lower)alkanoyl; or N-containing heterocycliccarbonyl optionally substituted with lower alkyl;

$R_f^1$ is aryl or a heterocyclic group, each of which is substituted with formyl, $R_g^1$ is aryl or a heterocyclic group, each of which is substituted with cyano, and $R^1$, $R^2$, $R^3$, and $R^4$ are each as defined above.

In the above and subsequent descriptions of the present specification, suitable examples of the various definitions to be included within the scope of the invention are explained in detail in the following.

The term "lower" is intended to mean a group having 1 to 6 carbon atom(s), unless otherwise provided.

Suitable "aryl" may be phenyl, naphthyl, phenyl substituted with lower alkyl [e.g. tolyl, mesityl, cumenyl, xylyl, diethylphenyl, diisopropylphenyl, di-tert-butylphenyl, etc.] or the like.

Suitable "halogen" is fluorine, chlorine, bromine and iodine.

Suitable "halo(lower)alkyl" may be chloromethyl, chloroethyl, bromomethyl, bromoethyl, fluoromethyl, dichloromethyl, difluoromethyl, trifluoromethyl or the like.

Suitable "lower alkyl" and lower alkyl moiety in the terms "lower alkylsulfonyl", "lower alkylsulfonylamino", "lower alkylsulfamoyl", "heterocyclic(lower)alkyl" and "lower alkoxy" may be straight or branched one having $C_1$–$C_6$ atoms such as methyl, ethyl, propyl, isopropyl, butyl, isobutyl, tert-butyl, pentyl, hexyl or the like, in which the preferable one is $C_1$–$C_4$ alkyl.

Suitable "lower alkanoyl" and lower alkanoyl moiety in the term "heterocyclic(lower)alkanoyl" may be formyl, acetyl, propionyl, butyryl, valeryl, pivaloyl or the like.

Suitable "hydroxy(lower)alkyl" may be hydroxymethyl, 1-hydroxyethyl, 1-hydroxypropyl and the like.

Suitable "halo(lower)alkanoyl" may be chloroacetyl, bromoacetyl, 3-chloropropionyl, 3-bromopropionyl and the like.

Preferable examples of "lower alkylsulfamoyl" may be N-methylsulfamoyl and N,N-dimethylsulfamoyl.

Suitable ester moiety in the term "esterified carboxy" may be lower alkyl ester [e.g. methyl ester, ethyl ester, propyl ester, isopropyl ester, butyl ester, isobutyl ester, hexyl ester, etc.], lower alkenyl ester [e.g. vinyl ester, allyl ester, etc.], lower alkynyl ester [e.g. ethynyl ester, propargyl ester, etc.] lower cycloalkyl ester [e.g. cyclopropyl ester, cyclobutyl ester, cyclohexyl ester, etc.], lower cycloalkenyl ester [e.g. cyclobutenyl ester, cyclopentenyl ester, cyclohexenyl ester, etc.], aromatic ester [e.g. phenyl ester, naphthyl ester, thienyl ester, furanyl ester, etc.], ar(lower)alkyl ester [e.g. benzyl ester, phenethyl ester, nitrobenzyl ester, thenyl ester, furfuryl ester, etc.] and the like.

Suitable "heterocyclic group" for $R^1$ and $R^4$ may be saturated or unsaturated N-, S- and/or O-containing heterocyclic group such as pyridyl, pyrimidinyl, pyrrolyl, pyrrolidinyl, imidazolyl, thiazolyl, thiadiazolyl, oxazolyl, thienyl, furyl, benzothiadiazolyl, benzoxadiazolyl, benzimidazolyl or the like.

Suitable heterocyclic moiety in the term "heterocyclic(lower)alkyl" may be saturated 5 or 6 membered N-, or N- and S-, or N- and O-containing heterocyclic group such as piperidyl, piperazinyl, morpholinyl, thiomorpholinyl, pyrrolidinyl, imidazolidinyl, pyrazolidinyl, oxazolidinyl or the like, which may be substituted with aforesaid lower alkyl etc..

Preferable examples of "heterocyclic(lower)alkyl" may be morpholino(lower)alkyl [e.g. morpholinomethyl, morpholinoethyl, morpholinopropyl, etc.], thiomorpholinomethyl, thiomorpholinoethyl, piperazinylmethyl, methyl substituted piperazinylmethyl, or the like.

Suitable N-containing heterocyclic moiety in the terms "N-containing heterocycliccarbonyl" and "N-containing heterocyclic(lower)alkyl" may be saturated 5 or 6 membered N-, or N- and S-, or N- and O-containing heterocyclic group such as 1-pyrrolidinyl, 1-imidazolidinyl, piperidino, 1-piperazinyl, morpholino, thiomorpholino, or the like.

The above "N-containing heterocyclic moiety" may optionally be substituted with a lower alkyl group as exemplified before.

Preferable examples of "N-containing heterocycliccarbonyl substituted with lower alkyl" may be 3-methylpiperidinocarbonyl, 4-methylpiperidinrcarbonyl, 4-methylpiperazin-1-ylcarbonyl, 2-ethylmorpholinocarbonyl, 2-isopropylthiomorpholin-4-ylcarbonyl, or the like.

Suitable salts of the compound [I] are conventional non-toxic pharmaceutically acceptable salts and may include an inorganic base salt such as an alkali metal salt [e.g. sodium salt, potassium salt, etc.], an alkaline earth metal salt [e.g. calcium salt, magnesium salt, etc.], an organic or inorganic acid addition salt [e.g. formate, acetate, fumarate, trifluoroacetate, maleate, tartrate, methanesulfonate, benzenesulfonate, toluenesulfonate, hydrochloride, hydrobromide, sulfate, phosphate, etc.], or the like.

With respect to the salts of the compounds [Ia] to [Iq] in the Processes 3 to 13, it is to be noted that these compounds are included within the scope of the compound [I], and accordingly the suitable examples of the salts of these compounds are to be referred to those as exemplified for the object compound [I].

The processes for preparing the object compounds [I]of the present invention are explained in detail in the following.

Process 1

The object compound [I] or its salt can be prepared by reacting a compound [II] or its salt with a compound [III] or its salt and ammonia or an agent which liberates ammonia (Step a), and then, if necessary, reacting the resultant mixture with an oxidizing agent (Step b).

Suitable salts of the compounds [II] and [III] may be the same as exemplified for the compound [I].

Step a

Suitable agents which liberate ammonia may be ammonium lower alkanoate [e.g. ammonium formate, ammonium acetate, ammonium propionate, ammonium butyrate, etc.], ammonium carbonate, ammonium hydrogencarbonate, ammonium carbamate or the like.

This reaction is usually carried out in a conventional solvent such as water, alcohol [e.g. methanol, ethanol, propanol, butanol, etc.], dioxane, tetrahydrofuran, methylene chloride, chloroform, dichloroethane, diethyl ether, benzene, acetone, ethyl acetate, propyl acetate, methyl ethyl ketone, methyl isobutyl ketone or any other organic solvent which does not adversely influence the reaction, or a mixture thereof.

The reaction temperature is not critical, and the reaction is usually carried out under cooling, at ambient temperature or under warming or heating.

In the reaction, a compound of the formula:

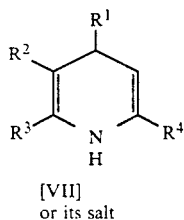

[VII]
or its salt wherein $R^1$, $R^2$, $R^3$ and $R^4$ are each as defined above, may be obtained according to reaction conditions and in that case, the compound [VII] or its salt is further subjected to oxidation reaction (step b) as mentioned below to give the compound [I] or its salt.

Step b

The oxidation reaction can be carried out by a conventional method which is applied for the transformation of an N-containing heterocyclic base to an aromatized N-containing heterocyclic compound, for example, by using an oxidizing agent such as manganese dioxide, lead tetraacetate, mercuric acetate, halogen [e.g. iodine, bromine, etc.], oxygen, hydrogen peroxide, nickel peroxide, sulfur powder, 2,3-dichloro-5,6-dicyano-1,4-benzoquinone, potassium permanganate, or the like.

The present reaction is usually carried out in a conventional solvent such as chloroform, methylene chloride, benzene, toluene, pyridine, ethyl acetate, propyl acetate, acetone, methyl ethyl ketone, methyl isobutyl ketone or any other organic solvent which does not adversely influence the reaction.

The reaction temperature is not critical and the reaction is preferably carried out at ambient temperature or under warming to heating.

Process 2

The object compound [I] or its salt can be prepared by reacting a compound [II] or its salt with a compound [IV] or its salt (Step a), and then, if necessary, reacting the resultant mixture with an oxidizing agent (Step b).

Step a

This reaction is usually carried out in a conventional solvent such as water, alcohol [e.g. methanol, ethanol, propanol, butanol, etc.], dioxane, tetrahydrofuran, methylene chloride, chloroform, dichloroethane, diethyl ether, benzene, acetone, ethyl acetate, propyl acetate, methyl ethyl ketone, methyl isobutyl ketone or any other organic solvent which does not adversely influence the reaction, or a mixture thereof.

This reaction is preferably carried out in the presence of Lewis acid [e.g. boron trifluoride etherate, etc.].

The reaction temperature is not critical, and the reaction is usually carried out under cooling, at ambient temperature or under warming or heating.

In this reaction, a compound [VII] or its salt as explained in the Process 1 Step a may be obtained according to reaction conditions and in that case, the compound [VII] or its salt is further subjected to oxidation reaction (step b) as mentioned below; to give the compound [I] or its salt.

Step b

This oxidation reaction mode and reaction conditions can be referred to those as explained in the above-mentioned Process 1 Step b.

Process 3

The object compound [Ib] or its salt can be prepared by reducing a compound [Ia] or its salt.

The reduction can be carried out by a conventional method, for instance, by chemical reduction and catalytic reduction.

Suitable reducing agents to be used in chemical reduction may be metallic compound [e.g. stannous chloride, etc.], lithium aluminum hydride, lithium triethoxyaluminum hydride or the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate. etc.], nickel catalysts [e.g. Raney nickel, etc.], and the like.

The reduction is usually carried out in a conventional solvent which does not adversely influence the reaction such as water, methanol, ethanol, propanol, formic acid, acetic acid, N,N-dimethylformamide, diethyl ether, dioxane, tetrahydrofuran, or a mixture thereof.

The reaction temperature of this reduction is not critical and the reaction is usually carried cut under cooling to heating.

Process 4

The object compound [Id] and its salt can ba prepared by subjecting a compound [Ic] or its salt to deesterification reaction.

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4,3,0]non-5-ene, 1,4-diazabicyclo[2,2,2]octane, 1,8-diazabicyclo[5,4,0]undec-7-ene, or the like. Suitable acid may include an organic acid [e.g. formic acid, acetic acid, propionic acid, trichloroacetic acid, trifluoroacetic acid, etc.] and an inorganic acid

[e.g. hydrochloric acid, hydrobromic acid, sulfuric acid, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 5

The object compound [If] or its salt can be prepared by subjecting a compound [Ie] or its salt to deesterification reaction.

This reaction can be carried out in substantially the same manner as Process 4, and therefore the reaction mode and reaction condition (e.g. solvent, reaction temperature, etc.) or this reaction are to be referred to those as explained in Process 4.

Process 6

The object compound [Ig] or its salt can be prepared by reacting a compound [Id] or its reactive derivative at the carboxy group or a salt thereof with a compound [V] or its salt.

Suitable salts of the compound [V] may be acid addition salt as exemplified for the compound [I].

As suitable said reactive derivatives at the carboxy group, there may be mentioned acid halides, acid anhydrides, active amides and esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and esters such as lower alkyl ester [e.g. methyl ester, ethyl ester, etc.], cyanomethyl ester, methoxymethyl ester, p-nitrophenyl ester, 2,4-dinitrophenyl ester, pentachlorophenyl ester, phenylazophenyl ester, carboxymethylthio ester, and N-hydroxysuccinimide ester.

The reaction is usually carried out in a conventional solvent, such as methylene chloride, chloroform, alcohol [e.g. methanol, ethanol, etc.], benzene, toluene, pyridine, diethyl ether, dioxane, tetrahydrofuran, acetone, acetonitrile, ethyl acetate, N,N-dimethylformamide or any other organic solvent which does not adversely affect the reaction. In case that the compound [V] is liquid, it can also be used as a solvent. In case that the compound [Ic] is used in the free acid form or salt form, it is preferable to carry out the reaction in the presence of a conventional condensing agent such as N,N'-dicyclohexylcarbodiimide, N-ethyl-N'-(3-dimethylaminopropyl)carbodiimide, phosphoryl chloride, phosphorus trichloride, thionyl chloride, oxalyl chloride, lower alkyl haloformate [e.g. ethyl chloroformate, isopropyl chloroformate, etc.], so-called Vilsmeier reagent prepared by the reaction of N,N-dimethylformamide with thionyl chloride, phosgene, trichloromethyl chloroformate, phosphoryl chloride, etc., or the like.

The reaction temperature is not critical and the reaction can be carried out under cooling, at ambient temperature, or under heating.

This reaction can typically be conducted in the presence or absence of an accelerator such as base.

Suitable base may include a tertiary amine [e.g. triethylamine, pyridine, N,N-dimethylaniline, etc.], an alkali metal hydroxide [e.g. sodium hydroxide, potassium hydroxide, etc. , an alkali metal carbonate [e.g. sodium carbonate, potassium carbonate, etc. , alkali metal bicarbonate [e.g. sodium bicarbonate, etc. , a slat of an organic acid [e.g. sodium acetate, etc. and the like. In case that the base is liquid, the base can be used as a solvent.

Process 7

The object compound [Ih] or its salt can be prepared by reacting a compound [If] or its reactive derivative at the carboxy group or a salt thereof with a compound [V] or its salt.

Suitable reactive derivative at the carboxy group of the compound [If] may be referred to those as explained in Process 6.

This reaction can be carried out in substantially the same manner as Process 6, and therefore the reaction mode and reaction condition (e.g. solvent, reaction temperature, etc.) of this reaction are to be referred to those as explained in Process 6.

Process 8

The object compound [Ii] or its salt can be prepared by subjecting a compound [Id] or its salt to azidation reaction in lower alkanol and then subjecting the resulting product to hydrolysis reaction.

(i) The first step

The reaction of this step can be carried out by reacting a compound [Id] or its salt with an azide compound such as sodium azide, diphenylphosphoryl azide or the like in lower alkanol [e.g. methanol, ethanol, propanol, butanol, t-butanol, etc.] under warming to heating. This reaction can optionally be accelerated in the presence of a base as exemplified in Process 6.

The reaction product of the first step is a compound of the following formula [VIII] and it can be subjected to the following second step with or without isolation and/or purification.

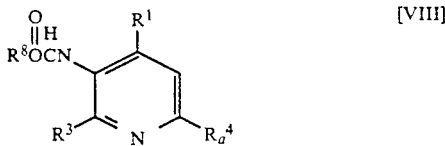

[wherein $R^8$ is lower alkyl, and $R^1$, $R^3$ and $R_a^4$ are each as defined above]

(ii) The second step

The compound [VIII] or its salt obtained in the first step is then subjected to hydrolysis reaction to give a compound [Ii] or its salt.

Suitable salts of the compound [VIII] may be the same as those exemplified for the compound [I].

This reaction can be carried out in substantially the same manner as the hydrolysis in Process 4, and therefore the reaction mode and reaction condition (e.g. solvent, reaction temperature. etc.) of this reaction are to be referred to those as explained in Process 4.

Process 9

The object compound [Ij] or its salt can be prepared by reacting a compound [Ii] or its salt with a compound [VI] or its reactive derivative at the carboxy group or a salt thereof.

Suitable reactive derivative at the carboxy group of the compound [VI] may be referred to those as explained in Process 6.

Suitable salts of the compound [VI] and its reactive derivative may be inorganic base salt as exemplified for the compound [I].

This reaction can be carried out in substantially the same manner as Process 6, and therefore the reaction mode and reaction condition (e.g. solvent, reaction temperature, etc.) of this reaction are to be referred to those as explained in Process 6.

Process 10

The object compound [Ik] or its salt can be prepared by reacting a compound [Ij] or its salt with a N-containing heterocyclic compound.

Suitable N-containing heterocyclic compound may be saturated 5 or 6 membered N-, or N- and S-, or N- and O-containing heterocyclic compound such as pyrrolidine, imidazolidine, piperidine, piperazine, N-(lower)alkylpiperazine [e.g. N-methylpiperazine, N-ethylpiperazine, etc.], morpholine, thiomorpholine, or the like.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

Process 11

The object compound [Im] or its salt can be prepared by reacting a compound [Il] or its salt with a reducing agent.

Suitable reducing agents to be used in the present reduction are a metal hydride compound such as aluminum hydride compound [e.g. lithium tri-t-butoxyaluminum hydride, etc.], borohydride compound [e.g. sodium borohydride, etc.], aluminum alkoxide [e.g. aluminum isopropoxide, etc.] or the like.

The reaction is usually carried out in a conventional solvent, such as water, alcohol [e.g. methanol, ethanol, propanol, isopropanol, etc.], chloroform, or any other organic solvent which does not adversely influence the reaction, or a mixture thereof.

The reaction temperature is not critical and the reaction can be carried out under cooling to heating.

Process 12

The object compound [Io] or its salt can be prepared by reacting a compound [In] or its salt with an oxidizing agent.

Suitable oxidizing agents may be Jones reagent, chromic acid, potassium permanganate, activated manganese dioxide, and the like.

This reaction is usually carried out in a solvent which does not adversely influence the reaction such as acetic acid, dichloromethane, acetone, ethyl acetate, chloroform or the like.

The reaction temperature is not critical, and the reaction is usually carried out under cooling to warming.

Process 13

The object compound [Iq] or its salt can be prepared by reacting a compound [Ip] or its salt with hydroxylamine and then reacting the resulting product with a dehydrating agent.

(i) The first step

The reaction of this step can be carried out by reacting a compound [Ip] or its salt with hydroxylamine.

This reaction is usually carried out in a conventional solvent such as N,N-dimethylformamide, tetrahydrofuran, dioxane, pyridine or any other organic solvent which does not adversely influence the reaction.

The reaction temperature is not critical and the reaction is usually carried out under cooling to heating.

(ii) The second step

The resulting product in the first step is then reacted with a dehydrating agent to give a compound [Iq] or its salt.

Suitable dehydrating agent may be phosphorus compound [e.g. phosphorus pentoxide, phosphorus pentachloride, phosphorus oxychloride, etc.], thionyl chloride, acid anhydride [e.g. acetic anhydride, etc.], phosgene, arylsulphonyl chloride [e.g. benzenesulfonyl chloride, p-toluenesulfonyl chloride, etc.], methanesulfonyl chloride, sulfamic acid, ammonium sulfamate, N,N'-dicyclohexylcarbodiimide, lower alkoxycarbonyl halide [e.g. ethyl chloroformate, etc.] and the like.

The reaction is usually carried out in a conventional solvent such as acetonitrile, methylene chloride, ethylene chloride, benzene, N,N-dimethylformamide, pyridine or any other organic solvent which does not adversely influence the reaction.

Additionally in case that the above-mentioned dehydrating agents are in liquid, they can also be used as a solvent.

The reaction temperature is not critical and the reaction is preferably carried out under warming or heating.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compounds [I] and their salts reduce the reperfusion injury and maintain the ATP content against the overload on the heart. Therefore, they are useful as drugs for ischemic diseases and as cardioprotective agents, especially drugs to improve or enhance the depressed cardiac metabolism, and are useful in the treatment of ischemic diseases, reperfusion injury and/or heart diseases [e.g. myocardial infarction, heart failure, angina pectoris, etc.].

The object compounds [I] and their salts of this invention can be used in a form of a conventional pharmaceutical preparation, for example, in solid, semisolid or liquid form, which contains an active substance of this invention in admixture with an organic or inorganic carrier or excipient suitable for external, oral or parenteral applications. The active ingredient may be compounded, for example, with the usual non-toxic, pharmaceutically acceptable carriers for tablets, pellets, capsules, patch, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing thickening and coloring agents and perfumes may be used. The pharmaceutical compositions can also contain preservative or bacteriostatic agents to keep the active ingredient in the desired preparations stable in activity. The active object compound is included in the pharmaceutical composition in the amount sufficient to produce the desired therapeutic effect upon the process of condition of diseases.

While a dosage of therapeutically effective amount of the object compound [I] of this invention varies according to the age and conditions of each individual patient to be treated, a daily dose of about 0.1–100 mg/kg, preferably 1 to 50 mg/kg of the active ingredient may be generally given for treating diseases.

The pharmaceutical compositions of this invention comprises, as an active ingredient, the compound [I] or its salt in an amount of about 0.2 mg to about 500 mg, per dosage unit for oral and parenteral use.

In order to show the usefulness of the object compound [I], the results of pharmacological tests are shown in the following.

Test Compounds (a)  3-(2-Morpholinoethylcarbamoyl)-2-methyl-4-(3-cyanophenyl)-6-phenylpyridine
(b)  4-(4-Amino-3-nitrophenyl)-2-methyl-3-(2-morpholinoethylcarbamoyl)-6-phenylpyridine
(c)  4-(4-Ethoxy-3-nitrophenyl)-2-methyl-3-(2-morpholinoethylcarbamoyl)-6-phenylpyridine The compounds (a) to (c) were dissolved in 2 equivalent of hydrochloric acid and used as Test Compounds.

Test

Method

The heart was isolated from male guinea-pig weighing 550–650 g and was perfused in the Langendorff mode at 37° C. at a constant perfusion pressure of 80 cm $H_2O$. The perfusion medium was Krebs-Henseleit bicarbonate solution containing 11 mM glucose. The solution was equilibrated with 95% $O_2$ and 5% $CO_2$ gas mixture at pH 7.4. A latex balloon was placed in the left ventricular cavity and then left ventricular systolic (LVSP) and diastolic (LVDP) pressure were measured. Heart rate (HR) was triggered by the pulse pressure. Coronary flow was monitored with electromagnetic flow probe placed on the aorta.

The heart was perfused for 45 min. with the perfusion medium and then for 15 min. with the perfusion medium containing the test compound. The heart was then subjected to the global ischemia by stopping the perfusion. After 35 min. of ischemia, the heart was reperfused by the perfusion medium containing no test compound. At the end of 40 min. reperfusion, the cardiac function was monitored. The heart was immidiately frozen for the estimation of ATP content.

Results

| Test Compound | Concentration (g/ml) | % change from control | | |
|---|---|---|---|---|
| | | Cardiac depression (pre-ischemia) LVSP × HR | Recovery of ATP content (% increase) | Coronary flow |
| (a) | $1 \times 10^{-6}$ | 4.0 | 89.2 | −2.0 |
| (b) | $1 \times 10^{-6}$ | −9.0 | 72.6 | 10.0 |
| (c) | $1 \times 10^{-6}$ | −3.2 | 97.8 | 8.4 |

The following Preparations and Examples are given for the purpose of illustrating the present invention in more detail.

Preparation 1

To a solution of acetophenone (7.4 g) and 4N-sodium hydroxide solution (16 ml) in ethanol (60 ml) was added 4-methyl-3-nitrobenzaldehyde (7.4 g) at ambient temperature under stirring and the resultant mixture was stirred at same condition for 1.5 hours. To the reaction mixture was added water and resulting precipitate was collected by filtration. The precipitate was dissolved in a mixture of ethyl acetate and tetrahydrofuran. The solution was washed with brine and dried over magnesium sulfate. The solvent was concentrated in vacuo and the crystalline residue was collected by filtration to give 3-(4-methyl-3-nitrophenyl)-1-phenyl-2-propen-1-one (10.25 g).

mp: 142°–144° C.
IR (Nujol): 1660, 1605, 1570, 1555, 1525 cm$^{-1}$.
NMR (DMSO-d$_6$, δ): 2.54 (3H, s), 7.55–7.83 (5H, m), 8.07–8.22 (4H, m), 8.53 (1H, d, J=2 Hz).
Mass (m/e): 267 (M+).

Preparation 2

The following compounds were obtained according to a similar manner to that of Preparation 1.

(1) 3-(4-Methoxy-3-nitrophenyl)-1-phenyl-2-propen-1-one (21.7 g) was obtained from 4-methoxy-3-nitrobenzaldehyde (18.1 g) and acetophenone (13.2 g).

mp: 143°–145° C.
IR (Nujol): 1655, 1615, 1600, 1578, 1525 cm$^{-1}$.
NMR (DMSO-d$_6$, δ): 4.01 (3H, s), 7.44 (1H, d, J=9 Hz), 7.55–7.72 (3H, m), 7.80 (1H, d, J=15.5 Hz), 8.06 (1H, d, J=15.5 Hz), 8.15–8.21 (3H, m), 8.53 (1H, d, J=2 Hz).
Mass (m/e): 283 (M+).

(2) 3-(4-Ethoxy-3-nitrophenyl)-1-phenyl-2-propen-1-one (17.8 g) was obtained from 4-ethoxy-3-nitrobenzaldehyde (19.5 g) and acetophenone (13.2 g).

mp: 125°–127° C.
IR Nujol): 1660, 1605, 1580, 1560, 1525, 1500 cm$^{-1}$.
NMR (DMSO-d$_6$, δ): 1.22 (3H, t, J=7 Hz), 4.32 (2H,q, J=7 Hz), 7.43 (1H, d, J=9 Hz), 7.58–8.46 (8H, m), 8.55 (1H, d, J=2 Hz).
Mass (m/e): 297 (M+).

(3) 3-(3-Cyanophenyl)-1-(3-chlorophenyl)-2-propen-1-one (6.3 g) was obtained from 3-cyanobenzaldehyde (6.6 g) and 3'-chloroacetophenone (9.3 g).

mp: 155°–157° C.
IR (Nujol): 2220, 1660, 1605, 1565 cm$^{-1}$.
NMR (DMSO-d$_6$, δ): 7.19–8.13 (9H m) 8.43 (1H,s).
Mass (m/e): 267 (M+).

(4) 3-(3-Nitrophenyl)-1-(4-hydroxyphenyl)-2-propen-1-one (7.6 g) was obtained from 3-nitrobenzaldehyde (15.1 g) and 4'-hydroxyacetophenone (13.6 g).

mp: 230°–232° C.
IR (Nujol): 1645, 1605, 1590, 1550 cm$^{-1}$.
NMR (DMSO-d$_6$, δ): 6.85 (2H, d, J=7 Hz), 7.52–7.86 (2H, m), 7.90–8.36 (5H, m), 8.65 (1H, d, J=2 Hz), 10.43 (1H, br s).

(5) 3-(3-Methylsulfonylphenyl)-1-phenyl-2-propen-1-one (0.77 g) was obtained from 3-methylsulfonylbenzaldehyde (0.58 g) and acetophenone (0.42 g).

IR (Nujol): 1660, 1600, 1560 cm$^{-1}$.
NMR (CDCl$_3$, δ): 3.11 (3H, s), 7.4–8.15 (10H, m), 8.25 (1H, s).
Mass (m/e): 286 (M+).

(6) 3-[3-(N-Methylsulfamoyl)phenyl]-1-phenyl-2-propen-1-one (3.81 g) was obtained from 3-(N-methylsulfamoyl)benzaldehyde (4.4 g) and acetophenone (2.65 g).

IR (Nujol): 3275, 1660, 1605, 1580 cm$^{-1}$.
NMR (CDCl$_3$, δ): 2.54 (3H, s), 7.25–8.25 (11H, m).
Mass (m/e): 301 (M+).

(7) 3-(3-Sulfamoylphenyl)-1-phenyl-2-propen-1-one (4.88 g) was obtained from 3-sulfamoylbenzaldehyde (5.5 g) and acetophenone (3.57 g).

IR (Nujol): 3320, 3220, 1655, 1600, 1570 cm$^{-1}$.
NMR (DMSO-d$_6$, δ): 7.2–8.45 (11H, m).
Mass (m/e): 287 (M+).

(8) 3-[3-(N,N-Dimethylsulfamoyl)phenyl]-1-phenyl-2-propen-1-one (0.9 g) was obtained from 3-(N,N-dimethylsulfamoyl)benzaldehyde (2.0 g) and acetophenone (1.13 g).

IR (Film): 1680, 1610, 1580 cm$^{-1}$.
NMR (CDCl$_3$, δ): 2.6 (3H, s), 2.76 (3H, s), 7.4–8.1 (11H, m).
Mass (m/e): 315 (M+).

Preparation 3

To a solution of acetophenone (7.2 g) and 4N-sodium hydroxide solution (14 ml) in ethanol (50 ml) was added 4-acetylamino-3-nitrobenzaldehyde (10.4 g) at ambient temperature under stirring and the resultant mixture was stirred at same condition for 2 hours. To the reaction mixture was added water and precipitate was collected by filtration. The precipitate was suspended in water (300 ml) and the resultant mixture was adjusted to pH 4.0 with 10% hydrochloric acid. The precipitate was collected by filtration and washed with brine and dried to give 3-(4-amino-3-nitrophenyl)-1-phenyl-2-propen-1-one (12.7 g).

mp: 245°–247° C. (dec.).
IR (Nujol): 3450, 3320, 1630, 1590, 1565, 1545, 1515 cm$^{-1}$.
NMR (DMSO-d$_6$, δ): 7.10 (1H, d, J=9 Hz), 7.32–8.30 (10H, m), 8.40 (1H. m).
Mass (m/e): 268 (M+).

Preparation 4

To a solution of 3-(6-carbamoyl-2-pyridyl)-1-phenyl-2-propen-1-one (0.5 g) in N,N-dimethylformamide (5 ml) was added phosphorus oxychloride (0.46 g) under ice-cooling. After stirring for 30 minutes at same temperature, the solution was poured into a mixture of ice-water (50 ml) and chloroform (10 ml). The resultant solution was adjusted to pH 9 with 4N-sodium hydroxide. The organic layer was washed with water and brine and dried over magnesium sulfate. After evaporating the solvent to give 3-(6-cyano-2-pyridyl)-1-phenyl-2-propen-1-one (0.38 g).

IR (Nujol): 2225, 1660, 1600, 1575 cm$^{-1}$.
NMR (CDCl$_3$, δ): 7.44–8.33 (10H, m).
Mass (m/e): 234 (M+).

Preparation 5

A mixture of 2-cyano-5-formylthiophene (4 g) and benzoylmethylenetriphenylphosphorane (11.09 g) in tetrahydrofuran (40 ml) was refluxed for 30 minutes. The reaction mixture was evaporated in vacuo to give 3-(5-cyano-2-thienyl)-1-phenyl-2-propen-1-one (3.95 g).

NMR (CDCl$_3$, δ): 7.21–8.12 (9H, M).
Mass (m/e): 239 (m+).

EXAMPLE 1

To a solution of 3-(3-cyanophenyl)-1-phenyl-2-propen-1-one (4.7 g) in methyl isobutyl ketone (50 ml) were added N-(2-morpholinoethyl)acetoacetamide (6.5 g) and ammonium acetate (2.3 g), and the mixture was stirred at 80° to 85° C. for 4 hours. After cooling, the reaction mixture was washed with water and dried over magnesium sulfate. To the filtrate containing 1,4-dihydro-3-(2-morpholinoethylcarbamoyl)-2-methyl-4-(3-cyanophenyl)-6-phenylpyridine and 3-(2-morpholinoethylcarbamoyl)-2-methyl-4-(3-cyanophenyl)-6-phenyl-pyridine was added manganese dioxide (20 g) and the resultant mixture was stirred at 80° to 85° C. for 1.5 hours. Manganese dioxide was filtered off, and the filtrate was concentrated in vacuo. The residue was dissolved in diluted hydrochloric acid and washed with ethyl acetate. The aqueous layer was adjusted to pH 8.0 with 20% aqueous solution of potassium carbonate, and extracted with ethyl acetate. The extract was washed with brine and dried over magnesium sulfate. The solvent was evaporated in vacuo, and the residue was subjected to a column chromatography on silica gel and eluted with a mixture of ethyl acetate and tetrahydrofuran (8:2 V/V). The fractions containing the desired compound were combined and concentrated in vacuo. The residue was recrystallized from diethyl ether to give 3-(2-morpholinoethylcarbamoyl)-2-methyl-4-(3-cyanophenyl)-6-phenylpyridine (2.55 g).

mp: 166°-168° C.

IR (Nujol): 3200, 2220, 1610, 1585, 1665, 1540 cm$^{-1}$.

NMR (DMSO-d$_6$, δ): 2.00–2.70 (6H, m), 2.67 (3H, s), 3.00–3.76 (6H, m), 7.38–8.60 (9H, m), 7.90 (1H, s).

Mass (m/e): 426 (M$^+$).

EXAMPLE 2

2-Methyl-3-(2-morpholinoethylcarbamoyl)-6-3-nitrophenyl)-4-phenylpyridine, which was obtained according to a similar manner to that of Example 1 from 1-(3-nitrophenyl)-3-phenyl-2-propen-1-one (3.8 g), N-(2-morpholinoethyl)acetoacetamide (5.8 g) and ammonium acetate (2.0 g), was treated with a solution of hydrogen chloride in methanol to give 2-methyl-3-(2-morpholinoethylcarbamoyl)-6-(3-nitrophenyl)-4-phenylpyridine dihydrochloride (1.92 g).

mp: 164°-165° C. (dec.).

IR (Nujol): 3330, 3180, 2300–2750, 1665, 1630, 1605, 1560, 1530 cm$^{-1}$.

NMR (DMSO-d$_6$, δ): 2.67 (3H, s), 2.60–4.0(12H, m), 7.23–7.63 (5H, m), 7.75 (1H, t, J=8 Hz), 7.97 (1H, s), 8.25 (1H, dd, J=2, 8 Hz), 8.57 (1H, d, J=8 Hz), 8.70–9.00 (2H, m).

EXAMPLE 3

The following compounds were obtained according to a similar manner to that of Example 1 or 2.

(1) 2-Methyl-3-(2-morpholinoethylcarbamoyl)-4,6-diphenylpyridine (1.6 g) from 1,3-diphenyl-2-propen-1-one (4.2 g), N-(2-morpholinoethyl)acetoacetamide (6.5 g) and ammonium acetate (2.3 g).

mp: 143°-145° C.

IR (Nujol): 3270, 1630, 1580, 1545 cm$^{-1}$.

NMR (DMSO-d$_6$, δ): 2.00–2.43 (6H, m), 2.63 (3H, s), 3.03–3.36 (2H, m), 3.40–3.70 (4H, m), 7.25–7.65 (8H, m), 7.70 (1H, s), 7.93–8.35 (3H, m).

(2) 2-Methyl-4-(2,3-dichlorophenyl)-3-(2-morpholinoethylcarbamoyl)-6-phenylpyridine (6.1 g) from 3-(2,3-dichlorophenyl)-1-phenyl-2-propen-1-one (11.6 g), N-(2-morpholinoethyl)acetoacetamide (13 g) and ammonium acetate (4.6 g).

mp: 126°-128° C.

IR (Nujol): 3250, 1630, 1570 cm$^{-1}$.

NMR (DMSO-d$_6$, δ): 1.83–2.40 (6H, m), 2.63 (3H, s), 2.85–3.35 (2H, m), 3.35–3.65 (4H, m), 7.20–7.53 (5H, m), 7.53–7.80 (1H, m), 7.72 (1H, s), 7.93–8.27 (3H, m).

(3) 2-Methyl-4-(3-chlorophenyl)-3-(2-morpholinoethylcarbamoyl)-6-phenylpyridine (2.73 g) from 3-(3-chlorophenyl)-1-phenyl-2-propen-1-one (5.1 g), N-(2-morpholinoethyl)acetoacetamide (6.5 g) and ammonium acetate (2.3 g).

mp: 159°-161° C.

IR (Nujol): 3200, 1610, 1585, 1565, 1540 cm$^{-1}$.

NMR (DMSO-d$_6$, δ): 1.90–2.40 (6H, m), 2.61 (3H, s), 2.90–3.36 (2H, m), 3.36–3.66 (4H, m), 7.16–7.50 (6H, m), 7.77 (1H, s), 7.95–8.40 (3H, m).

(4) 2-Methyl-4-(3-trifluoromethylphenyl)-3-(2-morpholinoethylcarbamoyl)-6-phenylpyridine (3.2 g) from 3-(3-trifluoromethylphenyl)-1-phenyl-2-propen-1-one (5.8 g), N-(2 TM morpholinoethyl)acetoacetamide (6.5 g) and ammonium acetate (2.3 g).

mp: 135°-137° C.

IR (Nujol): 3200, 1625, 1580, 1550 cm$^{-1}$.

NMR (DMSO-d$_6$, δ): 1.96–2.37 (6H, m), 2.63 (3H, s), 2.97–3.35 (2H, m), 3.35–3.62 (4H, m), 7.30–7.63 (3H, m), 7.63–7.95 (4H, m), 8.00–8.23 (2H, m), 7.80 (1H, s), 8.34 (1H, t, J=5 Hz).

(5) 2-Methyl-3-(2-morpholinoethylcarbamoyl)-4-2-nitro-4-thienyl)-6-phenylpyridine dihydrochloride (2.6 g) from 3-(2-nitro-4-thienyl)-1-phenyl-2-propen-1-one (3.9 g), N-(2-morpholinoethyl)acetoacetamide (4.9 g) and ammonium acetate (1.7 g).

mp: 265°-267° C. (dec.).

IR (Nujol): 3160, 2300–2750, 1665, 1630, 1605, 1580, 1550, 1530, 1500 cm$^{-1}$.

NMR (DMSO-d$_6$, δ): 2.67 (3H, s), 2.87–3.65 (6H, m), 3.53–4.07 (6H, m), 7.30–7.63 (3H, m), 8.00–8.26 (2H, m), 8.17 (1H, s), 8.33 (1H, d, J=2 Hz), 8.48 (1H, d, J=2 Hz), 9.20 (1H, t, J=5 Hz).

(6) 2-Methyl-3-(3-morpholinopropylcarbamoyl)-4-(3-nitrophenyl)-6-2-thienyl)pyridine dihydrochloride (1.95 g) from 3-(3-nitrophenyl)-1-(2-thienyl)-2-propen-1-one (5.2 g), N-(3-morpholinopropyl)acetoacetamide (6.85 g) and ammonium acetate (2.3 g).

mp: 180°-183° C. (dec.).

IR (Nujol): 3400, 3200, 2200–2750, 1670, 1625, 1600, 1530 cm$^{-1}$.

NMR (DMSO-d$_6$, δ): 1.53–2.03 (2H, m), 2.59 (3H, s), 2.70–3.45 (8H, m), 3.60–4.06 (4H, m), 7.15 (1H, dd, J=3, 5 Hz), 7.67 (1H, dd, J=2, 5 Hz , 7.73–8.35 (4H, m), 7.87 (1H, s), 8.33 (1H, d, J=2 Hz), 8.74 (1H, t, J=5 Hz).

(7) 2-Methyl-4-(4-nitrophenyl)-3-(3-morpholinopropylcarbamoyl)-6-(2-thienyl)pyridine dihydrochloride (2.0 g) from 3-(4-nitrophenyl)-1-(2-thienyl)-2-propen-1-one (5.2 g), N-(3-morpholinopropyl)acetoacetamide (6.85 g) and ammonium acetate (2.3 g).

mp: 130°-132° C. (dec.).

IR (Nujol): 3400, 3220, 2300–2750, 1625, 1600, 1510 cm$^{-1}$.

NMR (D$_2$O, δ): 1.63–2.10 (2H, m), 2.87 (3H, s), 2.97–4.53 (12H, m), 7.35 (1H, dd, J=5,5 Hz), 7.76 (2H, d, J=9 Hz), 7.87 (1H, s), 7.80–8.10 (2H, m), 8.38 (2H, d, J=9 Hz).

(8) 2-Methyl-4-(2-chlorophenyl)-3-(2-morpholinoethylcarbamoyl)-6-phenylpyridine dihydrochloride (1.3 g) from 3-(2-chlorophenyl)-1-phenyl-2-propen-1-one (5.1 g), N-(2-morpholinoethyl)acetoacetamide (6.5 g) and ammonium acetate (2.3 g).

mp: 186°-190° C. (dec.).

IR (Nujol): 3350, 3160, 2300–2750, 1665, 1630, 1605, 1555 cm$^{-1}$.

NMR (DMSO-d$_6$, δ): 2.80–3.70 (8H, m), 2.70 (3H, s), 3.70–4.03 (4H, m), 7.20–7.65 (4H, m), 7.83 (1H, s), 7.93–8.17 (2H, m), 8.17–8.45 (2H, m), 8.92 (1H, t, J=5 Hz).

(9) 2-Methyl-4-(3-chlorophenyl)-3-(4-methylpiperazin-1-ylcarbonyl)-6-phenylpyridine (2.1 g) from 3-(3-chlorophenyl)-1-phenyl-2-propen-1-one (5.1 g), 1-acetoacetyl-4-methylpiperazine (5.52 g) and ammonium acetate (2.3 g).

mp: 149°–151° C.

IR (Nujol): 1620, 1585, 1565, 1540 cm$^{-1}$.

NMR DMSO-d$_6$, δ): : 1.00–1.50 (1H, m), 2.00 (3H, s), 1.60–3.88 (7H, m), 2.50 (3H, s), 7.30–7.68 (7H, m), 7.80 (1H, s), 8.00–8.27 (2H, m).

(10) 2-Methyl-4-(2,3-dichlorophenyl)-3-(4-methylpiperazin-1-ylcarbonyl)-6-phenylpyridine dihydrochloride (1.8 g) from 3-(2,3-dichlorophenyl)-1-phenyl-2-propen-1-one (5.8 g), 1-acetoacetyl-4-methylpiperazine (5.52 g) and ammonium acetate (2.3 g).

mp 182°–185° C. (dec.).

IR (Nujol): 2100–2750, 1630, 1600, 1565 cm$^{-1}$.

NMR (D$_2$O, δ): 2.80–4.16 (7H, m), 3.06 (3H, s), 3.21 (3H, s), 4.50–5.00 (1H, m), 7.30–8.06 (9H, m).

(11) 2-Methyl-4-(3-nitrophenyl)-3-(2-morpholinoethylcarbamoyl)-6-(4-hydroxyphenyl)pyridine (1.96 g) from 3-(3-nitrophenyl)-1-(4-hydroxyphenyl)-2-propen-1-one (5.1 g), N-(2-morpholinoethyl)acetoacetamide (6.5 g) and ammonium acetate (2.3 g).

mp: 230°–231° C.

IR (Nujol): 3350, 1620, 1605, 1585, 1520 cm$^{-1}$.

NMR (DMSO-d$_6$, δ): 1 97–2.36 (6H, m), 2.56 (3H, s), 3.00–3.63 (6H, m), 6.82 (2H, d, J=9 Hz), 7.70 (1H, s), 7.57–8.43 (2H, m), 7.97 (2H, d, J=7 Hz), 8.10–8.43 (3H, m), 9.66 (1H, br s).

(12) 2-Methyl-4-(4-methyl-3-nitrophenyl)-3-(2-morpholinoethylcarbamoyl)-6-phenylpyridine (2.77 g) was obtained from 3-(4-methyl-3-nitrophenyl)-1-phenyl-2-propen-1-one (5.34 g), N-(2-morpholinoethyl)acetoacetamide (6.3 g) and ammonium acetate 2.3 g).

mp: 119°–122° C.

IR (Nujol): 3400, 1660, 1620, 1560, 1520 cm$^{-1}$.

NMR (DMSO-d$_6$, δ): 2.00–2.35 (6H, m), 2.57 (3H, s), 2.60 (3H, s), 2.95–3.36 (2H, m), 3.36–3.60 (4H, m), 7.25–7.90 (5H, m), 7.82 (1H, s), 7.97–8.25 (3H, m), 8.37 (1H, m).

(13) 4-(4-Methoxy-3-nitrophenyl)-2-methyl-3-(2-morpholinoethylcarbamoyl)-6-phenylpyridine (3.97 g) was obtained from 3-(4-methoxy-3-nitrophenyl)-1-phenyl-2-propen-1-one (5.66 g), N-(2-morpholinoethyl)acetoacetamide (6.3 g) and ammonium acetate (2.3 g).

mp: 160°–163° C.

IR (Nujol): 3400, 1660, 1620, 1570, 1530 cm$^{-1}$.

NMR (DMSO-d$_6$, δ): 2.05–2.40 (6H, m), 2.62 (3H, s), 3.07–3.63 (6H, m), 4.00 (3H, s), 7.27–7.57 (4H, m), 7.70–7.95 (1H, m), 7.81 (1H, s), 8.07–8.25 (3H, m), 8.37 (1H, m).

(14) 4-(4-Ethoxy-3-nitrophenyl)-2-methyl-3-(2-morpholinoethylcarbamoyl)-6-phenylpyridine (2.71 g) was obtained from 3-(4-ethoxy-3-nitrophenyl)-1-phenyl-2-propen-1-one (5.14 g), N-(2-morpholinoethyl)acetoacetamide (6.5 g) and ammonium acetate (2.3 g).

mp: 138°–141° C.

IR (Nujol): 3400, 1600, 1610, 1570, 1525 cm$^{-1}$.

NMR (DMSO-d$_6$, δ): 1.36 (3H, t, J=6 Hz), 2.03–2.46 (6H, m), 2.58 (3H, s), 3.00–3.63 (6H, m), 4.26 (2H, q, J=6 Hz), 7.25–7.63 (4H, m), 7.65–7.93 (1H, m), 7.80 (1H, s), 7.97–8.23 (3H, m), 8.35 (1H, m).

(15) 6-(3-Chlorophenyl)-4-(3-cyanophenyl)-2-methyl-3-(2-morpholinoethylcarbamoyl)pyridine (2.75 g) was obtained from 3-(3-cyanophenyl)-1-(3-chlorophenyl)-2-propen-1-one (5.34 g), N-(2-morpholinoethyl)acetoacetamide (6.5 g) and ammonium acetate (2.3 g).

mp: 178°–180° C. (dec.).

IR (Nujol): 3200, 2230, 1610, 1580, 1540 cm$^{-1}$.

NMR (DMSO-d$_6$, δ): 2.00–2.38 (6H, m), 2.60 (3H, s), 2.97–3.35 (2H, m), 3.35–3.63 (4H, m), 7.33–7.57 (3H, m), 7.76–8.03 (3H, m), 7.91 (1H, s), 8.03–8.26 (2H, m), 8.35 (1H, m).

(16) 4-(2-Furyl)-2-methyl-3-(2-morpholinoethylcarbamoyl)-6-phenylpyridine (1.67 g) was obtained from 3-(2-furyl)-1-phenyl-2-propen-1-one (4.0 g), N-2-morpholinoethyl)acetoacetamide (6.3 g) and ammonium acetate (2.3 g).

mp: 123°–125° C.

IR (Nujol): 3250, 1655, 1590, 1550 cm$^{-1}$.

NMR (DMSO-d$_6$, δ): 2.20–2.67 (6H, m), 2.56 (3H, s), 3.20–3.68 (6H, m), 6.63 (1H, dd, J=2, 4 Hz), 7.12 (1H, d, J=4 Hz), 7.30–7.60 (3H, m), 8.00–8.20 (2H, m), 7.84 (1H, d, J=2 Hz), 7.98 (1H, s), 8.50 (1H, m).

(17) 2-Methyl-4-(m-tolyl)-3-(2-morpholinoethylcarbamoyl)-6-phenylpyridine (2.3 g) was obtained from 3-(m-tolyl)-1-phenyl-2-propen-1-one (4.45 g), N-(2-morpholinoethyl)acetoacetamide (5.1 g) and ammonium acetate (2.3 g).

mp: 138°–140° C.

IR (Nujol): 3200, 1620, 1570, 1540 cm$^{-1}$.

NMR (DMSO-d$_6$, δ): 2.03–2.43 (6H, m), 2.37 (3H, s), 2.60 (3H, s), 3.00–3.63 (6H, m), 7.10–7.60 (7H, m), 7.73 (1H, s), 8.00–8.30 (3H, m).

(18) 4-(4-Amino-3-nitrophenyl)-2-methyl-3-(2-morpholinoethylcarbamoyl)-6-phenylpyridine (1.3 g) was obtained from 3-(4-amino-3-nitrophenyl)-1-phenyl-2-propen-1-one (6.2 g), N-(2-morpholinoethyl)acetoacetamide (6.5 g) and ammonium acetate (2.3 g).

mp: 190°–193° C.

IR (Nujol): 3430, 3300, 3220, 1625, 1585, 1550, 1510 cm$^{-1}$.

NMR (DMSO-d$_6$, δ): 2.06–2.40 (6H, m), 2.57 (3H, s), 3.05–3.60 (6H, m), 7.08 (1H, d, J=9 Hz), 7.33–7.73 (6H, m), 7.77 (1H, s), 8.00–8.47 (4H, m).

(19) 4-(3-Fluorophenyl)-2-methyl-3-(2-morpholinoethylcarbamoyl)-6-phenylpyridine (1.35 g) was obtained from 3-(3-fluorophenyl)-1-phenyl-2-propen-1-one (4.12 g), N-(2-morpholinoethyl)acetoacetamide (6.5 g) and ammonium acetate (2.3 g).

mp: 141°–142° C.

IR (Nujol): 3200, 1615, 1585, 1540 cm$^{-1}$.

NMR (DMSO-d$_6$, δ): 2.03–2.38 (6H, m), 2.60 (3H, s), 3.00–3.63 (6H, m), 7.10–7.60 (7H, m), 7.77 (1H, s), 8.00–8.40 (3H, m).

Mass (m/e): 419 (M+).

(20) 2-Methyl-3-(2-morpholinoethylcarbamoyl)-6-phenyl-4-(2-thienyl)pyridine (1.52 g) was obtained from 3-(2-thienyl)-1-phenyl-2-propen-1-one (4.28 g), N-(2-morpholinoethyl)acetoacetamide (6.3 g) and ammonium acetate (2.3 g).

IR (Nujol): 3200, 1620, 1570, 1540 cm$^{-1}$.

NMR (DMSO-d$_6$, δ): 2.17–2.60 (6H, m), 2.60 (3H, s), 3.23–3.67 (6H, m), 7.16 (1H, dd, J=2, 5 Hz), 7.43 (1H, d, J=2 Hz), 7.40–7.80 (4H, m), 7.82 (1H, s), 7.93–8.23 (2H, m), 8.49 (1H, m).

(21) 4-(4-Methoxy-3-nitrophenyl)-2-methyl-3-(3-morpholinopropylcarbamoyl)-6-phenylpyridine (2.48 g) was obtained from 3-(4-methoxy-3-nitrophenyl)-1-phenyl-2-propen-1-one (5.66 g), N-(3-morpholinopropyl)acetoacetamide (6.8 g) and ammonium acetate (2.3 g).

mp: 128°–130° C. (dec.).

IR (Nujol): 3350, 1650, 1620, 1590, 1525 cm$^{-1}$.

NMR (DMSO-d$_6$, δ): 1.20–1.60 (2H, m), 1.80–2.33 (6H, m), 2.57 (3H, s), 2.95–3.35 (2H, m), 3.35–3.63 (4H, m), 3.98 (3H, s), 7.25–7.55 (4H, m), 7.66–7.95 (1H, m), 7.80 (1H, s), 7.97–8.23 (3H, m), 8.38 (1H, m). (22) 6-(2-Furyl)-2-methyl-4-(3-nitrophenyl)-3-(3-morpholinopropylcarbamoyl)pyridine dihydrochloride (1.92 g)

was obtained from 3-(3-nitrophenyl)-1-(2-furyl)-2-propen-1-one (4.86 g), N-(3-morpholinopropyl)acetoacetamide (6.84 g) and ammonium acetate (2.3 g).

mp: 243°–245° C. (dec.).

IR (Nujol): 3220, 2720–2200, 1670, 1640, 1605, 1530 cm$^{-1}$.

NMR (DMSO-d$_6$, δ): 1.53–2.00 (2H, m), 2.65 (3H, s), 2.70–3.50 (8H, m), 3.73–4.07 (4H, m), 6.72 (1H, dd, J=2, 4 Hz), 7.48 (1H, d, J=4 Hz), 7.76 (1H, s), 7.73–8.08 (2H, m), 8.06–8.75 (3H, m), 8.90 (1H, m).

Mass (m/e): 450 (M+).

(23) 4-(3-Cyanophenyl)-2-methyl-3-(3-morpholinopropylcarbamoyl)-6-phenylpyridine dihydrochloride (2.85 g) was obtained from 3-(3-cyanophenyl)-1-phenyl-2-propen-1-one (4.67 g), N-(3-morpholinopropyl)acetoacetamide (6.8 g) and ammonium acetoacetate (2.3 g).

mp: 233°–235° C. (dec.).

IR (Nujol): 3200, 2220, 1650, 1620, 1605, 1575, 1550 cm$^{-1}$.

NMR (DMSO-d$_6$, δ): 1.56–2.03 (2H, m), 2.69 (3H, s), 2.65–3.50 (8H, m), 3.70–4.06 (4H, m), 7.30–8.30 (11H, m), 8.85 (1H, m).

(24) 4-(2-Fluoro-5-nitrophenyl)-2-methyl-3-(2-morpholinoethylcarbamoyl)-6-phenylpyridine (234 mg) was obtained from 3-(2-fluoro-5-nitrophenyl)-1-phenyl-2-propen-1-one (1.36 g), N-(2-morpholinoethyl)acetoacetamide (1.36 g) and ammonium acetate (0.46 g).

mp: 164°–166° C.

IR (Nujol): 3280, 1635, 1520, 1350 cm$^{-1}$.

NMR (CDCl$_3$, δ): 2.2–2.56 (6H, m), 2.73 (3H, s), 3.2–3.5 (2H, m), 3.52–3.8 (4H, m), 6.3 (1H, br), 7.13–7.6 (4H, m), 7.5 (1H, s), 7.85–8.45 (4H, m).

Mass (m/e): 464 (M+).

(25) 4-(5-Hydroxymethyl-2-furyl)-2-methyl-3-(2-morpholinoethylcarbamoyl)-6-phenylpyridine (4.4 g) was obtained from 3-(5-hydroxymethyl-2-furyl)-1-phenyl-2-propen-1-one (9.13 g), N-(2-morpholinoethyl)acetoacetamide (12.84 g) and ammonium acetate (4.6 g).

NMR (DMSO-d$_6$, δ): 2.30–2.55 (6H, m), 2.55 (3H, s), 3.37–3.60 (6H, m), 4.50 (2H, s), 6.47 (1H, d, J=4 Hz), 7.05 (1H, d, J=4 Hz), 7.43–7.72 (3H, m), 8.00 (1H, s), 8.08–8.13 (2H, m), 8.59 (1H, m)

(26) 4-(3-Nitro-4-propoxyphenyl)-2-methyl-3-(2-morpholinoethylcarbamoyl)-6-phenylpyridine (3.80 g) was obtained from 3-(3-nitro-4-propoxyphenyl)-1-phenyl-2-propen-1one (6.23 g), N-(2-morpholinoethyl)acetoacetamide (6.5 g) and ammonium acetate (2.3 g).

mp: 133.5°–136° C.

IR (Nujol): 3400, 1650, 1620, 1570, 1525 cm$^{-1}$.

NMR (DMSO-d$_6$, δ): 1.00 (3H, t, J=7 Hz), 1.53–1.90 (2H, m), 2.06–2.40 (6H, m), 2.58 (3H, s), 3.06–3.40 (2H, m), 3.40–3.63 (4H, m), 4.13 (2H, q, J=7 Hz), 7.27–7.60 (4H, m), 7.67–7.90 (1H, m), 7.78 (1H, s), 7.97–8.20 (3H, m), 8.31 (1H, m).

Mass (m/e): 504 (M+).

(27) 2-Methyl-4-(3-methylsulfonylphenyl)-3-(2-morpholinoethylcarbamoyl)-6-phenylpyridine dihydrochloride (2.17 g) was obtained from 3-(3-methylsulphonylphenyl)-1-phenyl-2-propen-1-one (4.35 g), N-(2-morpholinoethyl)acetoacetamide (4.89 g) and ammonium acetate (1.76 g).

mp: 200° C. (dec.).

IR (Nujol): 1660, 1630, 1605, 1300 cm$^{-1}$.

NMR (DMSO-d$_6$, δ): 2.65 (3H, s), 2.8–3.15 (4H, m), 3.2–4.0 (8H, m), 3.33 (3H, s), 7.43–8.27 (9H, m), 7.91 (1H, s), 8.95–9.1 (1H, m).

Mass (m/e): 479 (M+).

(28) 2-Methyl-4-[3-(N-methylsulfamoyl)phenyl]-3-(2-morpholinoethylcarbamoyl)-6-phenylpyridine dihydrochloride (2.7 g) was obtained from 3-[3-(N-methylsulfamoyl)phenyl]-1-phenyl-2-propen-1-one-(3.78 g), N-(2-morpholinoethyl)acetoacetamide (4.03 g) and ammonium acetate (1.45 g).

mp: 176° C. (dec.).

IR (Nujol): 1660, 1625, 1600, 1540 cm$^{-1}$.

NMR (DMSO-d$_6$, δ): 2.47 (3H, s), 2.65 (3H s), 2.7–4.0 (12H, m), 7.3–8.25 (9H, m), 7.94 (1H, s), 8.9–9.1 (1H, m).

Mass (m/e): 494 (M+).

(29) 2-Methyl-3-(2-morpholinoethylcarbamoyl)-6-phenyl-4-(3-sulfamoylphenyl)pyridine dihydrochloride (3.45 g) was obtained from 3-(3-sulfamoylphenyl)-1-phenyl-2-propen-1-one (3.6 g), N-(2-morpholinoethyl acetoacetamide (4.03 g) and ammonium acetate (1.45 g).

mp: 184° C. (dec.).

NMR (DMSO-d$_6$, δ): 2.65 (3H, s), 2.8–4.0 (12H, m), 7.31–8.3 (9H, m), 7.90 (1H, s), 9.0 (1H, m).

Mass (m/e): 480 (M+).

(30) 4-[3-(N,N-Dimethylsulfamoyl)phenyl]-2-methyl-3-(2-morpholinoethylcarbamoyl)-6-phenylpyridine dihydrochloride (2.18 g) was obtained from 3-[3-(N,N-dimethylsulfamoyl)phenyl]-1-phenyl-2-propen-1-one (5.0 g), N-(2-morpholinoethyl)acetoacetamide (5.1 g) and ammonium acetate (1.83 g).

mp: 207° C. (dec.).

IR (Nujol): 1660, 1625, 1600 cm$^{-1}$.

NMR (DMSO-d$_6$, δ): 2.68 (6H, s), 2.85–4.0 (12H, m) 7.4–8.25 (10H, m), 8.99 (1H, br).

Mass (m/e): 508 (M+).

(31) 4-(6-Cyano-2-pyridyl)-2-methyl-3-(2-morpholinoethylcarbamoyl)-6-phenylpyridine dihydrochloride (1.3 g) was obtained from 3-(6-cyano-2-pyridyl)-1-phenyl-2-propen-1-one (2.5 g), N-(2-morpholinoethyl)acetoacetamide (3.43 g) and ammonium acetate (1.23 g).

mp: 150°–152° C.

IR (Nujol): 3350 (br), 3200, 2225, 1670, 1635, 1540 cm$^{-1}$.

NMR (DMSO-d$_6$, δ): 2.64 (3H, s), 2.91–4.05 (12H, m), 7.42–7.64 (3H, m), 8.05–8.35 (6H, m), 8.89 (1H, br).

Mass (m/e): 427 (M+).

(32) 4-(5-Cyano-2-thienyl)-2-methyl-3-(2-morpholinoethylcarbamoyl)-6-phenylpyridine dihydrochloride (1.96 g) was obtained from 3-(5-cyano-2-thienyl)-1-phenyl-2-propen-1-one (2.0 g), N-(2-morpholinoethyl)acetoacetamide (2.69 g) and ammonium acetate (0.97 g).

mp: 241°–245° C.

IR (Nujol): 3160, 2220, 1670, 1620, 1600, 1545 cm$^{-1}$.

NMR (DMSO-d$_6$, δ): 2.61 (3H, s), 2.96–4.2 (12H, m), 7.46–8.31 (8H, m), 9.2 (1H, t, J=5.4 Hz).

Mass (m/e): 432 (M+).

EXAMPLE 4

To a solution of N-(2-morpholinoethyl)-3-aminocrotonamide (12.1 g) in 1,2-dichloroethane (120 ml) was dropwise added a mixture of 3-(2-methoxy-5-methylsulfonylphenyl)-1-phenyl-2-propen-1-one (6 g) in 1,2-dichloroethane (60 ml) and boron trifluoride etherate (2.3 ml) under refluxing. After refluxed for 21 hours, the reaction mixture was poured into water (120 ml) and adjusted to pH 1 with 10% hydrochloric acid. To the separated aqueous layer was added ethyl acetate (120 ml), and the mixture was adjusted to pH 9. The separated organic layer containing 1,4-dihydro-2-methyl-4-(2-methoxy-5-methylsulfonylphenyl)-3-(2-morpholinoethylcarbamoyl)-6-phenylpyridine and 2-methyl-4-(2-methoxy-5-methylsulfonylphenyl)-3-(2-morpholinoethylcarbamoyl)-6-phenylpyridine was dried over magnesium sulfate and manganese dioxide (12 g) was added thereto. The reaction mixture was refluxed for 3 hours, insoluble material was filtered off and the filtrate was concentrated under reduced pressure. The residue was subjected to a column chromatography on silica gel eluting with a mixture of chloroform and methanol (50:1 V/V). The fractions containing the object compound were combined and evaporated in vacuo. The residue was recrystallized from ethanol to give 2-methyl-4-(2-methoxy-5-methylsulfonylphenyl)-3-(2-morpholinoethylcarbamoyl)-6-phenylpyridine (1.6 g).

IR (Nujol): 3290, 1618, 1500 cm$^{-1}$.

NMR (DMSO-$d_6$, $\delta$): 2.0–2.3 (6H, m), 2.58 (3H, s), 3.0–3.6 (6H, m), 3.14 (3H, s), 3.8 (3H, s), 7.2–8.2 (10H, m).

EXAMPLE 5

The following compounds were obtained according to a similar manner to that of Example 4.

(1) 2-Methyl-4-(3-methylsulfonylaminophenyl)-3-(2-morpholinoethylcarbamoyl)-6-phenylpyridine (1.1 g) was obtained from N-(2-morpholinoethyl)-3-aminocrotonamide (5.3 g) and 3-(3-methylsulfonylaminophenyl)-1-phenyl-2-propen-1-one (5 g).

mp: 92°–95° C.

IR (CHCl$_3$): 3370, 1640 cm$^{-1}$.

NMR (CDCl$_3$, $\delta$): 2.2–2.6 (6H, m), 2.8 (3H, s), 3.16 (3H, s), 3.3–4.0 (6H, m), 6.2–6.6 (1H, m), 7.4–7.7 (8H, m), 8.0–8.3 (2H, m).

Mass (m/e): 494 (M$^+$).

(2) 4-(2,3-Dichlorophenyl)-2-methyl-3-(2-morpholinoethylcarbamoyl)-6-phenylpyridine (1.2 g) was obtained from N-(2-morpholinoethyl)-3-aminocrotonamide (5.8 g) and 3-(2,3-dichlorophenyl)-1-phenyl-2-propen-1-one (5 g).

mp: 119°–121° C.

IR (Nujol): 3200, 1615, 1550 cm$^{-1}$.

NMR (DMSO-$d_6$, $\delta$): 1.9–2.4 (6H, m), 2.6 (3H, s), 2.9–3.8 (6H, m), 7.2–8.3 (10H, m).

Mass (m/e): 470 (M$^+$).

(3) 4-(2,1,3-Benzoxadiazol-4-yl)-2-methyl-3-(2-morpholinoethylcarbamoyl)-6-phenylpyridine (1.15 g) was obtained from N-(2-morpholinoethyl)-3-aminocrotonamide (7.59 g) and 3-(2,1,3-benzoxadiazol-4-yl)-1-phenyl-2-propen-1-one (6.85 g).

mp: 145°–146° C.

IR (Nujol): 3220, 1625, 1560, 1310, 1110 cm$^{-1}$.

NMR (CDCl$_3$, $\delta$): 2.0–2.5 (6H, m), 2.76 (3H, s), 3.03–3.9 (6H, m), 6.1–6.57 (1H, m), 7.3–8.25 (8H, m).

Mass (m/e): 443 (M$^+$).

(4) 2-Methyl-3-(2-morpholinoethylcarbamoyl)-4-(3-nitrophenyl)-6-(2-thienyl)pyridine dihydrochloride (1.1 g) was obtained from N-(2-morpholinoethyl)-3-aminocrotonamide (5.3 g) and 3-(3-nitrophenyl)-1-(2-thienyl)-2-propen-1-one (5 g).

mp: 248°–250° C. (dec.).

IR (Nujol): 3160, 2420, 1650, 1600, 1510 cm$^{-1}$.

NMR (DMSO-$d_6$, $\delta$): 2.77 (3H, s), 3.0–3.9 (8H, m), 3.9–4.2 (4H, m), 7.3–7.5 (1H, m), 7.8–8.3 (5H, m), 8.4–8.6 (2H, m), 9.13 (1H, t, J=5 Hz).

Mass (m/e): 452 (free M$^+$).

(5) 6-(2-Furyl)-2-methyl-3-(2-morpholinoethylcarbamoyl)-4-(3-nitrophenyl)pyridine (1.2 g) was obtained from N-(2-morpholinoethyl)-3-aminocrotonamide (5.7 g) and 3-(3-nitrophenyl)-1-(2-furyl)-2-propen-1-one (5 g).

mp: 133°–134° C.

IR (Nujol): 3490, 3300, 1630, 1520 cm$^{-1}$.

NMR (CDCl$_3$, $\delta$): 2.3–2.7 (6H, m), 2.9 (3H, s), 3.3–3.9 (6H, m), 6.35 (1H, br), 6.76 (1H, dd, J=4, 2 Hz), 7.35 (1H, d, J=4 Hz), 7.73 (1H, s), 7.7–7.8 (1H, m), 7.85 (1H, d, J=2,8 Hz), 8.1 (1H, dt, J=2, 8 Hz), 8.46 (1H, dt, J=2, 8 Hz), 8.5–8.6 (1H, m).

Mass (m/e): 436 (M$^+$).

(6) 3-(2-Morpholinoethylcarbamoyl)-2-methyl-4-(3-cyanophenyl)-6-phenylpyridine.

mp: 166°–168° C.

Mass (m/e): 426 (M$^+$).

(7) Benzyl 4-(3-cyanophenyl)-2,6-dimethyl-3-pyridinecarboxylate (6.5 g) was obtained from benzyl 3-aminocrotonate (15.4 g) and 4-(3-cyanophenyl)-3-buten-2-one (11.5 g).

IR (Nujol): 2225, 1720, 1585, 1550 cm$^{-1}$.

NMR (CDCl$_3$, $\delta$): 2.54 (6H, s), 5.06 (2H, s), 6.9–7.7 (10H, m).

Mass (m/e): 342 (M$^+$). (8) Benzyl 4-(3-cyanophenyl)-2-methyl-6-phenyl-3-pyridinecarboxylate (25.32 g) was obtained from benzyl 3-aminocrotonate (19.35 g) and 3-(3-cyanophenyl)-1-phenyl-2-propen-1-one (19.67 g).

IR (Film): 2230, 1720, 1580, 1545 cm$^{-1}$.

NMR (CDCl$_3$, $\delta$): 2.72 (3H, s), 5.12 (2H, s), 7.0–8.15 (15H, m).

Mass (m/e): 404 (M$^+$). (9) Ethyl 3-acetyl-2-methyl-4-(3-nitrophenyl)-6-pyridinecarboxylate (1.47 g) was obtained from 4-amino-3-penten-2-one (0.99 g) and ethyl 4-(3-nitrophenyl)-2-oxo-3-butenoate (2.5 g).

NMR (CDCl$_3$, $\delta$): 1.46 (3H, t, J=7 Hz), 2.12 (3H, s), 2.67 (3H, s), 4.52 (2H, q, J=7 Hz), 7.6–7.8 (2H, m), 8.01 (1H, s), 8.25–8.44 (2H, m).

Mass (m/e): 328 (M$^+$). (10) Ethyl 4-(3-cyanophenyl)-6-methoxycarbonyl-2-methyl-3-pyridinecarboxylate (1.57 g) was obtained from ethyl 3-aminocrotonate (1.08 g) and methyl 4-(3-cyanophenyl)-2-oxo-3-butenoate (1.8 g).

IR (Nujol): 3400, 2225, 1720, 1660, 1575 cm$^{-1}$.

NMR (CDCl$_3$, $\delta$): 1.11 (3H, t, J=7 Hz), 2.73 (3H, s), 4.03 (3H, s), 4.22 (2H, q, J=7 Hz), 7.45–8.07 (5H, m).

Mass (m/e): 324 (M$^+$). (11) Ethyl 5-cyano-6-methyl-4-(3-nitrophenyl)-2-pyridinecarboxylate (2.78 g) was obtained from 2-amino-1-propenecarbonitrile (1.65 g) and ethyl 4-(3-nitrophenyl)-2-oxo-3-butenoate (5.0 g).

IR (Nujol): 2220, 1740, 1575, 1520, 1350 cm$^{-1}$.

NMR (CDCl$_3$, $\delta$): 1.47 (3H, t, J=7 Hz), 2.99 (3H, s), 4.55 (2H, q, J=7 Hz), 7.79 (1H, t, J=8 Hz), 7.9–8.09 (1H, m), 8.11 (1H, s , 8.3–8.6 (2H, m).

Mass (m/e): 311 (M$^+$). (12) Diethyl 6-methyl-4-(3-nitrophenyl)-2,5-pyridinedicarboxylate (3.45 g) was obtained from ethyl 3-aminocrotonate (1.71 g) and ethyl 4-(3-nitrophenyl)-2-oxo-3-butenoate (3.0 g).

NMR (CDCl$_3$, $\delta$): 1.15 (3H, t, J=7 Hz), 1.47 (3H, t, J=7 Hz), 2.8 (3H, s), 4.24 (2H, q, J=7 Hz), 4.54 (2H, q, J=7 Hz), 7.5–8.0 (1H, m), 7.78 (1H, s), 8.02 (1H, s), 8.15–8.5 (2H, m).

EXAMPLE 6

A mixture of 4-{3-cyanophenyl)-2-methyl-3-(2-morpholinoethylcarbamoyl)-6-phenylpyridine (1.5 g) and Raney's Nickel (1.5 g) in 75% formic acid (40 ml) was refluxed for one hour under stirring. The reaction mixture was filtered and the filtrate was evaporated in vacuo. The residue was dissolved in a mixture of ethyl acetate and water and the resultant solution was adjusted to pH 8.0 with 20% aqueous potassium carbonate. The separated organic layer was washed with brine and dried over magnesium sulfate. The solvent was evaporated in vacuo and the residue was subjected to a column chromatography on silica gel and eluted with a mixture of ethyl acetate and diisopropyl ether (8:2 V/V). The eluted solution was evaporated in vacuo and the residue was recrystallized from a mixture of ethyl acetate and diisopropyl ether to give 4-(3-formylphenyl)-2-methyl-3-(2-morpholinoethylcarbamoyl)-6-phenylpyridine (0.8 g).

mp: 122°–125° C.

IR (Nujol): 3180, 1690, 1600, 1580, 1535 cm$^{-1}$.

NMR (DMSO-d$_6$, $\delta$): 2.00–2.35 (6H, m), 2.60 (3H, s), 2.97–3.35 (2H, m), 3.35–3.60 (4H, m), 7.30–8.23 (9H, m), 7.80 (1H, s), 8.33 (1H, m), 10.05 (1H,s).

EXAMPLE 7

A solution of benzyl 4-(3-cyanophenyl)-2,6-dimethyl-3-pyridinecarboxylate (0.45 g) in a mixture of ethanol (9 ml) and tetrahydrofuran (9 ml) was hydrogenated under an atmospheric pressure of hydrogen over 10% palladium charcoal (90 mg) at 60° C. for 1.5 hours. After removal of the catalyst, the solvent was evaporated in vacuo. The residue was triturated with diethyl ether and dried to give 4-(3-cyanophenyl)-2,6-dimethyl-3-pyridinecarboxylic acid (0.25 g).

IR (Nujol) : 3400 (br), 2225, 1680, 1610 cm$^{-1}$.

NMR (DMSO-d$_6$, $\delta$): 2.48 (3H, s), 2.5 (3H, s), 7.16–8.0 (4H, m).

Mass (m/e): 252 (M$^+$).

EXAMPLE 8

The following compound was obtained according to a similar manner to that of Example 7.

4-(3-cyanophenyl)-2-methyl-6-phenyl-3-pyridinecarboxylic acid (6.75 g) was obtained from benzyl 4-(3-cyanophenyl)-2-methyl-6-phenyl-3-pyridinecarboxylate (15.0 g).

NMR (DMSO-d$_6$, $\delta$): 2.64 (3H, s), 7.3–8.4 (10H, m).

Mass (m/e): 314 (M$^+$).

EXAMPLE 9

To a solution of ethyl 5-cyano-6-methyl-4-(3-nitrophenyl)-2-pyridinecarboxylate (2.75 g) in ethanol (30 ml) was added a solution of sodium hydroxide (0.37 g) in water (6 ml). After the mixture was stirred at ambient temperature for 1.5 hours, the reaction mixture was adjusted to pH 2 with 6N hydrochloric acid. The resulting precipitates were filtered off, washed with water, and dried to give 5-cyano-6-methyl-4-(3-nitrophenyl)-2-pyridinecarboxylic acid (2.4 g).

IR (Nujol): 2220, 1705, 1520, 1350 cm$^{-1}$.

NMR (DMSO-d$_6$, $\delta$): 2.84 (3H, s), 7.8–8.65 (4H, m), 8.1 (1H, s).

Mass (m/e) : 283 (M$^+$).

EXAMPLE 10

The following compounds were obtained according to a similar manner to that of Example 9. (1) 5-Acetyl-6-methyl-4-(3-nitrophenyl)-2-pyridinecarboxylic acid (0.98 g) was obtained from ethyl 5-acetyl-6-methyl-4-(3-nitrophenyl)-2-pyridinecarboxylate (1.4 g).

NMR (DMSO-d$_6$, $\delta$): 2.18 (3H, s), 2.54 (3H, s), 7.7–7.9 (2H, m), 7.96 (1H, s), 8.14–8.42 (2H, m).

Mass (m/e): 300 (M$^+$). (2) 4-(3-Cyanophenyl)-5-ethoxycarbonyl-6-methyl-2-pyridinecarboxylic acid (0.22 g) was obtained from ethyl 4-(3-cyanophenyl)-6-methoxycarbonyl-2-methyl-3-pyridinecarboxylate (0.5 g).

NMR (DMSO-d$_6$, $\delta$): 1.01 (3H, t, J=7 Hz), 2.6 (3H, s), 4.15 (2H, q, J=7 Hz), 7.4–8.2 (4H, m), 7.97 (1H, s).

Mass (m/e): 310 (M$^+$). 3) 5-Ethoxycarbonyl-6-methyl-4-(3-nitrophenyl)-2-pyridinecarboxylic acid (1.40 g) was obtained from diethyl 6-methyl-4-(3-nitrophenyl)-2,5-pyridinedicarboxylate (1.7 g).

NMR (CDCl$_3$, $\delta$): 1.17 (3H, t, J=7 Hz), 2.8 (3H, s), 4.28 (2H, q, J=7 Hz), 7.5–8.0 (2H, m), 8.17 (1H, s), 8.2–8.6 (2H, m), 9.32 (1H, s).

EXAMPLE 11

To a solution of thionyl chloride (0.29 g) in methylene chloride (5 ml) was added N,N-dimethylformamide (0.18 g) at 10° C. and the mixture was stirred at the same temperature for 1 hour. Thereto was added 2,6-dimethyl-4-(3-cyanophenyl)-3-pyridinecarboxylic acid (0.505 g) at 10° C. and the mixture was stirred at ambient temperature for 1 hour. To the resulting mixture was added dropwise a solution of 2-morpholinoethylamine (0.62 g) in methylene chloride (2 ml) at 10° C. The mixture was stirred at the same temperature for 1.5 hours, diluted with methylene chloride (10 ml) and a saturated aqueous solution of sodium bicarbonate (10 ml). The separated organic layer was washed with water and brine, dried and concentrated under reduced pressure. The residue was purified by column chromatography on silica gel (20 g) eluting with a mixture of chloroform and methanol (25:1 V/V). The fractions containing the desired compound were combined and concentrated in vacuo. The residue was tritulated with diethyl ether to give 4-(3-cyanophenyl)-2,6-dimethyl-3-(2-morpholinoethylcarbamoyl)pyridine (0.33 g).

mp: 158°–161° C.

IR (Nujol): 3525, 3360, 3260, 2230, 1635, 1590, 1540 cm$^{-1}$.

NMR (CDCl$_3$, $\delta$) : 2.15–2.34 (6H, m), 2.60 (3H, s), 2.63 (3H, s), 3.21–3.39 (2H, m), 3.46–3.63 (4H, m), 6.0 (1H, br), 7.0 (1H, s), 7.47–7.82 (4H, m).

Mass (m/e) : 364 (M$^+$).

EXAMPLE 12

Ethyl 2-methyl-6-(2-morpholinoethylcarbamoyl)-4-(3-nitrophenyl)-3-pyridinecarboxylate, which was obtained according to a similar manner to that of Example 11 from 5-ethoxycarbonyl-6-methyl-4-(3-nitrophenyl)-2--pyridinecarboxylic acid (1.3 g) and 2-morpholinoethylamine (1.28 g), was treated with a solution of hydrogen chloride in ethanol to give ethyl 2-methyl-6-(2-morpholinoethylcarbamoyl)-4-(3-nitrophenyl)-3-pyridinecarboxylate dihydrochloride (1.2 g).

mp: 142°–143° C. (dec.).

IR (Nujol): 1720, 1670, 1620, 1585, 1520, 1350 cm$^{-1}$.

NMR (CDCl$_3$, $\delta$): 1.14 (3H, t, J=7 Hz), 2.73–4.53 (12H, m), 4.23 (2H, q, J=7 Hz), 7.5–8.5 (5H, m), 10.42 (1H, br), 11.95 (1H, br).

Mass (m/e): 442 (free M$^+$).

EXAMPLE 13

A mixture of 4-(3-cyanophenyl)-2-methyl-6-phenyl-3-pyridinecarboxylic acid (3.7 g), diphenylphosphoryl azide (3.24 g), triethylamine (1.19 g) and t-butanol (35 ml) was refluxed for 5 hours. After the organic solvent was evaporated, chloroform (40 ml) and a saturated aqueous solution of sodium bicarbonate (40 ml) were added to the residue. The separated organic layer was washed with water and brine, dried and concentrated in vacuo. The residue containing 3-(t-butoxycarbonylamino)-4-(3-cyanophenyl)-2-methyl-6-phenylpyridine was dissolved with ethanol (35 ml). After conc. hydrochloric acid (2 ml) was added to the solution at 0° C., the mixture was stirred at 0° C. for 1.5 hours and further at 80° C. for 7.5 hours. The mixture was concentrated, dissolved with chloroform (40 ml) and water (40 ml) and adjusted to pH 9 with 5N sodium hydroxide. The organic layer was separated, washed with brine, dried and concentrated in vacuo. The residue was purified by column chromatography on silica gel (70 g) eluting with a mixture of chloroform and methanol (100:1 V/V). The fractions containing the desired compound were combined and concentrated in vacuo. The residue was triturated with diethyl ether to give 3-amino-4-(3-cyanophenyl)-2-methyl-6-phenylpyridine (1.30 g).

IR (Nujol): 3460, 3380, 2225, 1620 cm$^{-1}$.

NMR (CDCl$_3$, δ): 2.57 (3H, s), 3.72 (2H, s), 7.2-8.0 (10H, m).

Mass (m/e): 285 (M+).

EXAMPLE 14

To a solution of 3-amino-4-(3-cyanophenyl)-2-methyl-6-phenylpyridine (0.6 g) and pyridine (0.2 g) in toluene (10 ml) was added 3-chloropropionyl chloride (0.32 g) at 0° C. The mixture was stirred at the same temperature for 30 minutes and further at ambient temperature for 6 hours. After the mixture was allowed to stand at ambient temperature for 3 days, N,N-dimethylformamide (10 ml) was added thereto to dissolve the precipitates. The mixture was stirred at ambient temperature for 5 hours, diluted with ice-cold water (50 ml) and ethyl acetate (50 ml), and adjusted to pH 10 with 5N sodium hydroxide. The separated organic layer was washed with brine, dried and concentrated in vacuo. The residue was triturated with diisopropyl ether to give 3-(3-chloropropionylamino)-4-(3-cyanophenyl)-2-methyl-6-phenylpyridine (0.48 g).

IR (Nujol): 3230, 2230, 1650, 1520 cm$^{-1}$.

NMR (CDCl$_3$, δ): 2.63 (3H, s), 2.69 (2H, t, J=6 Hz), 3.79 (2H, t, J=6 Hz), 6.94 (1H, s), 7.35-7.8 (8H, m), 7.9-8.1 (2H, m).

Mass (m/e): 375 (M+).

EXAMPLE 15

The following compound was obtained according to a similar manner to that of Example 14.

3-Chloroacetylamino-4-(3-cyanophenyl)-2-methyl-6-phenylpyridine (0.4 g) was obtained from 3-amino-4-(3-cyanophenyl)-2-methyl-6-phenylpyridine (0.6 g) and chloroacetyl chloride (0.28 g).

IR (Nujol): 3280, 2230, 1705, 1515 cm$^{-1}$.

NMR (CDCl$_3$, δ): 2.64 (3H, s), 4.07 (2H, s), 7.35-8.10 (11H, m).

Mass (m/e): 361 (M+).

EXAMPLE 16

A mixture of 3-(3-chloropropionylamino)-4-(3-cyanophenyl)-2-methyl-6-phenylpyridine (0.45 g) and morpholine (0.23 g) in a mixture of methylene chloride (5 ml) and tetrahydrofuran (10 ml) was refluxed for 8 hours. The mixture was concentrated, diluted with water (20 ml) and chloroform (20 ml). The separated organic layer was washed with water, dried and concentrated in vacuo. The residue was triturated with diethyl ether to give 4-(3-cyanophenyl)-2-methyl-3-(3-morpholinopropionylamino)-6-phenylpyridine (0.45 g).

mp: 150.5°-152° C.

IR (Nujol): 2225, 1670, 1590, 1505 cm$^{-1}$.

NMR (CDCl$_3$, δ): 2.3-2.64 (8H, m), 2.62 (3H, s), 3.4-3.62 (4H, m), 7.35-8.1 (10H, m), 10.23 (1H, s).

Mass (m/e): 426 (M+).

EXAMPLE 17

The following compound was obtained according to a similar manner to that of Example 16.

4-(3-Cyanophenyl)-2-methyl-3-morpholinoacetylamino-6-phenylpyridine (0.28 g) was obtained from 3-chloroacetylamino-4-(3-cyanophenyl)-2-methyl-6-phenylpyridine (0.37 g) and morpholine (0.2 g).

mp: 160.5°-161.5° C.

IR: Nujol): 3300, 2230, 1680, 1490 cm$^{-1}$.

NMR (CDCl$_3$, δ): 2.35-2.55 (4H, m), 2.61 (3H, s), 3.03 (2H, s), 3.55-3.72 (4H, m), 7.35-8.1 (10H, m), 8.62 (1H, s).

Mass (m/e): 412 (M+).

EXAMPLE 18

To a solution of 5-acetyl-6-methyl-4-(3-nitrophenyl)-2-pyridinecarboxylic acid (0.95 g) in tetrahydrofuran (10 ml) was added N-hydroxybenzotriazole (0.43 g) and N-ethyl-N'-(3-dimethylaminopropyl)carbodiimide hydrochloride (0.61 g) at 5° C. After the mixture was stirred at the same temperature for 1 hour, 2-morpholinoethylamine (0.41 g) and triethylamine (0.32 g) was added thereto. The mixture was stirred at ambient temperature for 2 hours and diluted with ice-cold water (20 ml) and ethyl acetate (20 ml). The separated organic layer was washed with brine, dried and concentrated in vacuo. The residue was triturated with diethyl ether to give 3-acetyl-2-methyl-6-(2-morpholinoethylcarbamoyl)-4-(3-nitrophenyl)pyridine (0.45 g).

mp: 107°-110° C.

IR (Nujol): 3320, 1690, 1665, 1515, 1340 cm$^{-1}$.

NMR (CDCl$_3$, δ): 2.10 (3H, s), 2.4-2.7 (6H, m), 2.61 (3H, s), 3.51-3.85 (6H, m), 7.6-7.8 (2H, m), 8.09 (1H, s), 8.26-8.4 (2H, m), 8.46 (1H, br).

Mass (m/e): 412 (M+).

EXAMPLE 19

The following compound was obtained according to a similar manner to that of Example 18.

3-Cyano-2-methyl-4-(3-nitrophenyl)-6-(2-morpholinoethylcarbamoyl)pyridine (1.23 g) was obtained from 5-cyano-6-methyl-4-(3-nitrophenyl)-2-pyridinecarboxylic acid (2.3 g) and 2-morpholinoethylamine (1.06 g).

mp: 154°-155° C.

IR (Nujol): 3370, 2220, 1680, 1610, 1530, 1510 cm$^{-1}$.

NMR (CDCl$_3$, δ): 2.4-2.8 (6H, m), 2.94 (3H, s), 3.5-3.9 (6H, m), 7.7-8.1 (2H, m), 8.22 (1H, s), 8.33-8.63 (3H, m).

Mass (m/e): 395 (M+).

EXAMPLE 20

Ethyl 4-(3-cyanophenyl)-2-methyl-6-(2-morpholinoethylcarbamoyl)-3-pyridinecarboxylate, which was obtained according to a similar manner to that of Example 18 from 4-(3-cyanophenyl)-5-ethoxycarbonyl-6-methyl-2-pyridinecarboxylic acid (0.93 g) and 2-morpholinoethylamine (0.39 g), was treated with a solution of fumaric acid (0.54 g) in ethanol (11 ml) to give ethyl 4-(3-cyanophenyl)-2-methyl-6-(2-morpholinoethylcarbamoyl)-3-pyridinecarboxylate fumarate (0.84 g).

mp: 161°-163° C. (dec.).

IR (Nujol): 3300, 2225, 1720, 1670, 1525 cm$^{-1}$.

NMR (DMSO-d$_6$, δ): 1.0 (3H, t, J=7 Hz), 2 24-2.7 (6H, m), 2.63 (3H, s), 3.35-3.7 (6H, m), 4.16 (2H, q, J=7 Hz), 6.62 (2H, s), 7.63-7.85 (2H, m), 7.92 (1H, s), 7.86-8.1 (2H, m), 8.82 (1H, t, J=6 Hz).

Mass (m/e): 422 (free M$^+$).

EXAMPLE 21

To a solution of 3-acetyl-2-methyl-6-(2-morpholinoethylcarbamoyl)-4-(3-nitrophenyl)pyridine (3 g) in methanol (30 ml) was added sodium borohydride (0.28 g) under ice-cooling. After stirring for 1 hour at same temperature, the solution was poured into a mixture of ice water (50 ml) and chloroform (50 ml). The organic layer was washed with brine and dried over magnesium sulfate. After evaporating the solvent, the residue was recrystallized from a mixture of ethanol and ethyl acetate to give 3-(1-hydroxyethyl)-2-methyl-6-(2-morpholinoethylcarbamoyl)-4- (3-nitrophenyl)pyridine (1.53 g).

mp: 166°-167° C.

IR (Nujol): 3370, 3325, 3070, 1650, 1590, 1525, 1350 cm$^{-1}$.

NMR (CDCl$_3$, δ): 1.53 (3H, d, J=7 Hz), 2.4-2.73 (6H, m), 2.87 (3H, s), 3.45-3.85 (6H, m). 5.0-5.18 (1H, m), 7.53-7.71 (2H, m) 7.76 (1H, s), 8.1-8.38 (2H, m), 8.49 (1H, br).

Mass (m/e): 414 (M$^+$).

EXAMPLE 22

A mixture of 4-(5-hydroxymethyl-2-furyl)-2-methyl-3-(2-morpholinoethylcarbamoyl)-6-phenylpyridine (4.4 g) and activated manganese dioxide (26 g) in ethyl acetate (100 ml) was refluxed for 3 hours under stirring. Manganese dioxide was filtered off and the filtrate was evaporated in vacuo and the residue was subjected to column chromatography on silica gel. The column was eluted with a mixture of ethyl acetate and tetrahydrofuran (7:3 V/V) and the fraction was evaporated in vacuo. The residue was crystallized from a mixture of ethyl acetate and diisopropyl ether to give 4-(5-formyl-2-furyl)-2-methyl-3-(2-morpholinoethylcarbamoyl)-6-phenylpyridine (1.2 g).

NMR (DMSO-d$_6$, δ): 2.39-2.60 (6H, m), 2.60 (3H, s), 3.39-3.66 (6H, m), 7.41 (1H, d, J=4 Hz), 7.67 (1H, d, J=4 Hz), 7.42-7.69 (3H, m), 8.14 (1H, s) 8.13-8.18 (2H, m), 8.65 (1H, m), 9.70 (1H, s).

EXAMPLE 23

A solution of 4-(5-formyl-2-furyl)-2-methyl-3-(2-morpholinoethylcarbamoyl)-6-phenylpyridine (1.2 g) and hydroxylamine hydrochloride (0.26 g) in a mixture of N,N-dimethylformamide (5 ml) and pyridine (4 ml) was stirred at ambient temperature for 2.5 hours. To the reaction mixture was added acetic anhydride (5 ml) and the resulting solution was stirred at 80° C. for 1 hour. The mixture was poured into a mixture of water and ethyl acetate and adjusted to pH 1.0 with 10% hydrochloric acid. The separated aqueous layer was adjusted to pH 8.0 with 20% aqueous potassium carbonate and extracted with ethyl acetate. The extract was washed with brine and dried over magnesium sulfate. The solvent was evaporated in vacuo and the residue was subjected to column chromatography on silica gel. The column was eluted with a mixture of ethyl acetate and tetrahydrofuran (85:15 V/V) and the fraction was evaporated in vacuo. The residue was recrystallized from a mixture of ethyl acetate and diisopropyl ether to give 4-(5-cyano-2-furyl)-2-methyl-3-(2-morpholinoethylcarbamoyl)-6-phenylpyridine (0.66 g).

mp: 141°-143° C. IR (Nujol): 3220, 2230, 1655, 1600, 1540 cm$^{-1}$. NMR (DMSO-d$_6$, δ): 2.33-2.73 (6H, m), 2.63 (3H, s) 3.30-3.80 (6H, m), 7.40-7.60 (3H, m), 7.40 (1H, d, J=4 Hz), 7.77 (1H, d, J=4 Hz), 8.13 (1H, s), 8.10-8.70 (2H, m), 8.60 (1H, m).

What we claim is:

1. A compound of the formula:

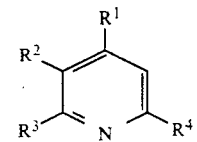

wherein
R$^1$ is aryl optionally substituted with substituents(s) selected from the group consisting of nitro, cyano, halogen, halo(lower)alkyl, lower alkoxy, lower alkylsulfonyl, lower alkylsulfonylamino, amino, lower alkanoyl, sulfamoyl and lower alkylsulfamoyl;

R$^2$ is carbamoyl substituted with heterocyclic(lower)alkyl;

R$^3$ is lower alkyl; and

R$^4$ is aryl optionally substituted with substituent(s) selected from the group consisting of nitro, hydroxy and halogen;

provided that R$^4$ is aryl substituted with substituent(s) selected from the group consisting of nitro and hydroxy when R$^1$ is phenyl substituted with nitro, or its pharmaceutically acceptable salt.

2. A compound of claim 2, wherein
R$^1$ is aryl substituted with cyano,
R$^2$ is carbamoyl substituted with heterocyclic(lower)alkyl and
R$^4$ is aryl.

3. A compound of claim 2, wherein
R$^1$ is phenyl substituted with cyano,
R$^2$ is carbamoyl substituted with morpholino(lower)alkyl and
R$^4$ is phenyl.

4. A compound of claim 3, which is 3-(2-morpholinoethylcarbamoyl)-2-methyl-4-(3-cyanophenyl)-6-phenylpyridine.

5. A cardioprotective pharmaceutical composition comprising an effective amount of a compound of claim 1, as an active ingredient, in association with a pharmaceutically acceptable, substantially nontoxic carrier or excipient.

6. A method for therapeutic treatment of ischemic diseases, depressed cardiac metabolism, reperfusion injury or heart diseases which comprise administering an effective amount of a compound of claim 1 to a human being or animal.

* * * * *